United States Patent [19]

Schirmer et al.

[11] 4,227,007

[45] Oct. 7, 1980

[54] DIURETHANES

[75] Inventors: Ulrich Schirmer, Heidelberg; Wolfgang Rohr, Mannheim; Bruno Wuerzer; Kurt Fett, both of Limburgerhof, all of Fed. Rep. of Germany

[73] Assignee: BASF Aktiengesellschaft, Fed. Rep. of Germany

[21] Appl. No.: 869,323

[22] Filed: Jan. 13, 1978

[30] Foreign Application Priority Data

Jan. 31, 1977 [DE] Fed. Rep. of Germany ....... 2703838

[51] Int. Cl.$^2$ ...................... C07C 125/04; A01N 9/20
[52] U.S. Cl. ........................................ 560/25; 71/103; 71/104; 71/105; 71/111; 260/346.22; 260/397.7 R; 260/397.7 D; 260/454; 260/456 A; 260/465 D; 424/228; 424/229; 424/285; 424/300; 560/22; 560/26; 560/13; 560/18
[58] Field of Search .............................. 560/25, 22, 26

[56] References Cited

U.S. PATENT DOCUMENTS

| 3,036,112 | 5/1962 | Lynn | 71/111 |
|---|---|---|---|
| 3,142,699 | 7/1964 | Wagner et al. | 560/26 |
| 3,297,745 | 1/1967 | Fekete et al. | 560/26 |
| 3,470,232 | 9/1969 | Duennenberger et al. | 560/25 |
| 3,632,530 | 1/1972 | Kinoshita | 560/26 |
| 3,721,700 | 3/1973 | Schuierer | 560/26 |
| 3,751,370 | 8/1973 | Stimberg et al. | 560/25 |
| 3,867,426 | 2/1975 | Olin et al. | 560/29 |
| 3,869,504 | 3/1975 | Boroschewski et al. | 560/29 |
| 3,901,936 | 8/1975 | Boroschewski | 560/29 |
| 3,904,669 | 9/1975 | Boroschewski et al. | 560/29 |
| 3,923,870 | 12/1975 | Singer | 560/25 |
| 3,954,770 | 5/1976 | Mayerhoefer et al. | 560/25 |
| 3,979,202 | 9/1976 | Olin et al. | 560/29 |
| 4,061,864 | 12/1977 | Guthrie et al. | 560/26 |

OTHER PUBLICATIONS

Akopyan et al., Chem. Abstracts, vol. 74, 112492(w), 1971.
Hidehiko et al., "Chem. Absts.," 82, 72946(d), 1975.

*Primary Examiner*—G. T. Breitenstein
*Attorney, Agent, or Firm*—Keil & Witherspoon

[57] ABSTRACT

New and valuable diurethanes having a good herbicidal action, herbicides containing these compounds, and a process for controlling the growth of unwanted plants with these compounds.

9 Claims, No Drawings

DIURETHANES

The present invention relates to new and valuable diurethanes having a herbicidal action, herbicides containing these compounds, and a process for controlling the growth of unwanted plants with these compounds.

It is known to use 2-sec-butyl-4,6-dinitrophenol (U.S. Pat. No. 2,192,197), ethyl-N-(3-N'-phenylcarbamoyloxy)-phenyl)-carbamate and methyl-N-(3-(N'-(3'-methylphenylcarbamoyloxy)-phenyl)-carbamate (German Printed Application DAS 1,567,151), 3-isopropyl-2,1,3-benzothiadiazin-(4)-one-2,2-dioxide (German Printed Application DAS No. 1,542,836), and 1-phenyl-4-amino-5-chloropyridazone-(6) (German No. 1,105,232) as herbicides. These compounds are established herbicides with special areas of application.

We have now found that new diurethanes of the formula

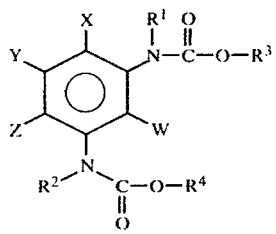

where $R^1$ and $R^2$ are identical or different and each denotes hydrogen, alkyl (e.g., methyl, ethyl, isopropyl), alkoxyalkyl (e.g., methoxymethyl, 2-methoxyethyl), haloalkyl (e.g., chloromethyl), unsubstituted benzyl, or benzyl substituted by alkyl or halogen, $R^3$ and $R^4$ are identical or different and each denotes unsubstituted alkyl, alkyl substituted by halogen, alkoxy or substituted or unsubstituted aryl (e.g., methyl, ethyl, 2-chloroethyl, 2-methoxyethyl, benzyl, isopropyl, n-propyl, 4-chlorobenzyl, n-butyl, sec.-butyl, tert.-butyl, isobutyl, 2,4-dichlorobenzyl, 2-ethylhexyl, n-decyl), unsubstituted or halogen-substituted alkenyl (e.g., allyl, 2-chloropropen-(1)-yl-(3), buten-(1)-yl-(3)), unsubstituted or halogen- or alkoxy-substituted alkynyl (e.g., propargyl, butyn-(1)-yl-(3), 1-chlorobutyn-(2)-yl-(4)), unsubstituted or alkyl-substituted cycloalkyl (e.g. cyclopentyl, cyclohexyl, 3-methylcyclohexyl, 2,6-dimethylcyclohexyl, cycloheptyl, 4-tert.-butylcyclohexyl, cyclooctyl, cyclododecyl, 3,5-dimethylcyclohexyl), bicycloalkyl (e.g., norbornyl), tricycloalkyl (e.g., tricyclo[4,3,1$^{2,5}$0$^{1,6}$]-decyl), phenyl with fused ring system (e.g., naphthyl, benzofuranyl, indyl), phenyl, mono- or polysubstituted phenyl with the substituents alkyl, haloalkyl, alkoxyalkyl, cycloalkyl, halogen, alkoxy, haloalkoxy, alkoxycarbonylalkoxy, nitro, amino, aryl, aryloxy, thiocyanate, cyano,

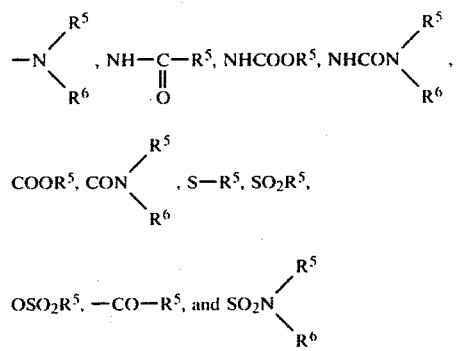

(e.g., phenyl, 4-fluorophenyl, 2-methoxyphenyl, 3-methylphenyl, 2-fluorophenyl, 3-methyl-5-isopropylphenyl, 3-ethylphenyl, 3-chlorophenyl, 2,4,6-trimethylphenyl, 3-fluorophenyl, 3-chloro-4-fluorophenyl, 3,4-dimethylphenyl, 3-trifluoromethylphenyl, 4-methylphenyl, 3,4-difluorophenyl, 3-chloro-4-methylphenyl, 3-bromophenyl, 4-iodophenyl, 4-chlorophenyl, 2-chlorophenyl, 2-chloro-4-fluorophenyl, 3-isopropylphenyl, 4-ethylphenyl, 3-methoxycarbonylaminophenyl, 4-ethoxyphenyl, 2-methylphenyl, 3-methoxyphenyl, 4-cyanophenol, 2,6-dimethylphenyl, 2,4-dichlorophenyl, 3-methyl-4-chlorophenyl, 2-trifluoromethylphenyl, 2,4-dibromophenyl, 4-trifluoromethylphenyl, 4-methoxyphenyl, and 3-(1'-ethoxycarbonylethoxy)-phenyl), $R^5$ and $R^6$ being identical or different and each denoting hydrogen, unsubstituted or mono- or polysubstituted aryl, or one of the two substituents having the meanings given for $R^1$, and W, X, Y and Z are identical or different and each denotes hydrogen, alkyl (e.g., methyl), haloalkyl (e.g., trifluoromethyl), alkoxy (e.g., methoxy), halogen (fluoro, chloro, bromo, iodo), nitro or amino, have a good herbicidal action on numerous unwanted plants and are well tolerated by many crop plants. The new compounds also have a fungicidal action.

The new compounds may for example be prepared by the following methods; the radicals W, X, Y, Z, $R^1$, $R^2$, $R^3$ and $R^4$ have the above meanings.

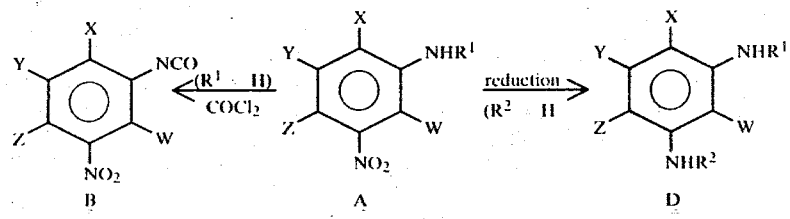

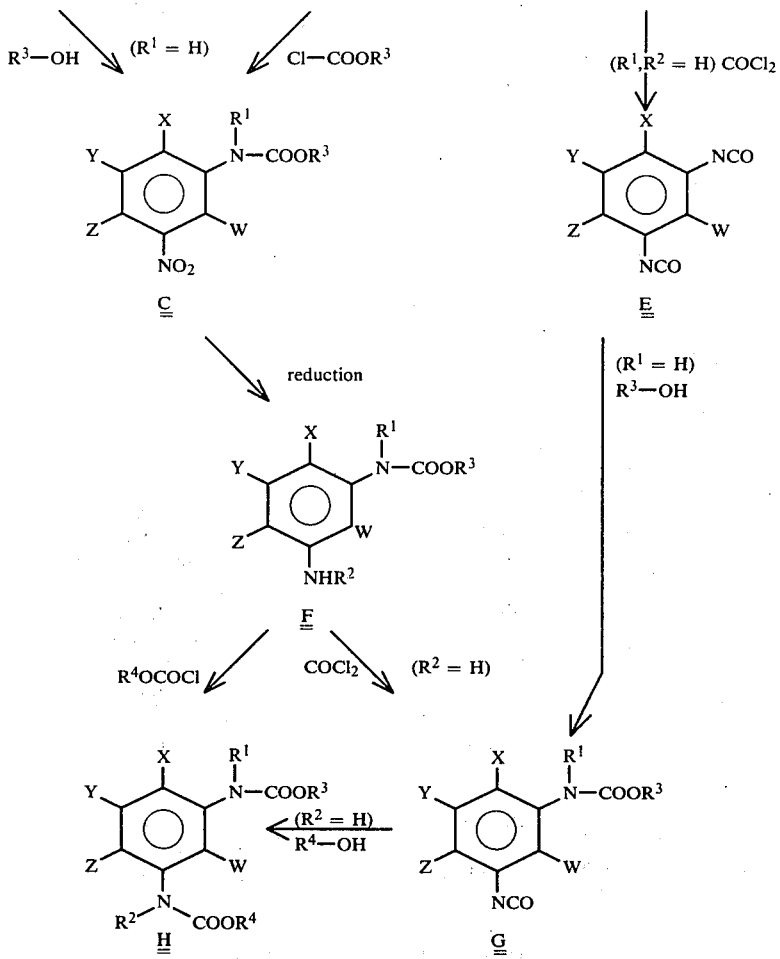

This reaction scheme clearly illustrates the interrelationship between the starting materials. It is also clear that, depending on the nature of the substituents W, X, Y, Z, $R^1$, $R^2$, $R^3$ and $R^4$ and on the availability of the reactants, one route or another may be advantageous. The reaction of F to give H is preferred.

Starting from prior art meta-nitroanilines (A), meta-nitrophenyl isocyanates (B) may be prepared (W. Siefkin, J. Liebigs Annalen der Chemie, 562, 75 et seq., 1949) which in turn react smoothly with the hydroxy components $R^3$—OH to give the nitrourethanes (C) (S. Petersen, Methoden der Organ. Chemie, VIII, 131, Georg-Thieme-Verlag, Stuttgart, 4th ed., 1952), which are, however, also accessible direct from the meta-nitroanilines (A) and chloroformates ($R^3O$—CO—Cl) (German Laid-Open Application DOS 1,643,763). Subsequent reduction gives the amino compounds (F; $R^2$=H) (S. Schroter, Methoden der Organ. Chemie, XI/1, 360 et seq., Georg-Thieme-Verlag, Stuttgart, 4th ed., 1957) which are reacted, either direct or after conversion into the product mono-substituted on the amino nitrogen (F; $R^2 \neq H$) (Methoden der Organ. Chemie, XI/1, 24 et seq., Georg-Thieme-Verlag, Stuttgart, 4th ed., 1957) with chloroformates ($R^4O$—CO—Cl), to give the desired diurethanes (H) (German Laid-Open Application DOS 1,643,763). The aminourethanes (F) may also be obtained by reaction of meta-phenylenediamines (D) with chloroformates. A further synthesis possibility is the reaction of aryl-1,3-diisocyanates (E) with only 1 mole of the hydroxy component $R^3$—OH; this reaction gives the isocyanatourethanes (G) (J. A. Parker, J. J. Thomas and C. L. Zeise, J. Org. Chem., 22, 594–596, 1957), which are also obtainable by phosgenating the aminourethanes (F) (German Laid-Open Application DOS 1,914,270, p. 5, Ex. 8). Subsequent reaction with the hydroxyl component $R^4$OH gives the desired end products. In principle, the —COOR$^3$ or —COOR$^4$ groupings may be introduced in any order.

The preferred synthesis stages are described in more detail below:

(a) The 3-nitrophenyl isocyanates (B) are reacted with or without a catalyst usually used for isocyanate reactions, e.g., tertiary amines (triethylamine, 1,4-diazabicyclo-(2,2,2)-octane), nitrogenous heterocycles (pyridine, 1,2-dimethylimidazole) or organic tin compounds (dibutyl tin diacetate, dimethyl tin dichloride), in the presence or absence of a solvent inert under the reaction conditions, e.g., hydrocarbons (ligroin, naphtha, toluene, pentane, cyclohexane), halohydrocarbons (methyl chloride, chloroform, dichloroethane, chlorobenzene, o-, m- and p-dichlorobenzene), nitrohydrocarbons (nitrobenzene, nitromethane), nitriles (acetonitrile, butyronitrile, benzonitrile), ethers(diethyl ether, tetrahydrofuran, dioxane), esters (ethyl acetate, methyl propionate), ketones (acetone, methyl ethyl ketone) or amides (dimethylformamide, foramamide) (German Laid-Open Application DOS 1,568,138), at temperatures of from 0° to 150° C., preferably from 40° to 100° C.

(b) 3-nitroanilines (A) are reacted with a chloroformate in a suitable solvent, e.g., water, alcohols (methanol, ethanol, isopropanol) or those given under (a), with the additional employment of a conventional acid binder, e.g., alkali metal hydroxides, carbonates, bicarbonates, alkaline earth metal oxides, hydroxides, carbonates, bicarbonates, and tertiary organic bases (e.g., triethylamine, pyridine, N.N-dimethylaniline, N,N-dimethylcyclohexylamine, quinoline, tributylamine) or starting material 3-nitroaniline, at temperatures of from −20° to +150° C., preferably from +20° to 80° C.

(c) The nitrourethanes (C) may be reduced by one of the prior art processes, e.g., by catalytic hydrogenation, by a metal/acid combination, e.g., a combination of iron and acid, by a metal/alcohol combination, e.g., zinc dust/aqueous alcohol, iron/aqueous alcohol, etc.

(d) For the reaction of the m-phenylenediamines (D), comparable conditions as for (b) apply; it may, however, be advantageous to employ an excess of m-phenylenediamine.

(e) The aminourethanes F are reacted with chloroformates analogously to (b); the solution obtained for example by catalytic hydrogenation of the nitrourethanes C may also be employed direct without further purification.

The preparation of the new diurethanes and their precursors is illustrated by the following examples.

I Nitrourethanes

EXAMPLE A

At 20° to 25° C. and while stirring, a mixture of 85 parts by weight of 3-nitrophenyl isocyanate and 43 parts by weight of toluene (absolute) is metered into a solution of 64.3 parts by weight of 4-chlorophenol and 3 parts by weight of triethylamine in 430 parts by weight of toluene (absolute).

To complete the reaction, the mixture was stirred for 1 hour at room temperature. After cooling to 0° C., the reaction product was suction filtered; m.p.: 137°–138° C.

The compound has the following structural formula:

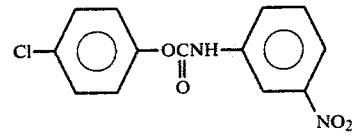

EXAMPLE B 17.4 parts of sodium bicarbonate is added to 26 parts by weight of 3-nitro-N-methylaniline in 320 parts by weight of ethyl acetate. While stirring, 33 parts by weight of m-tolyl chloroformate is slowly added, the mixture is stirred for 20 hours at room temperature and filtered, the solvent is removed in vacuo, and the residue which remains is recrystallized from toluene/cyclohexane; m.p.: 114°–116° C.

The compound has the following structural formula:

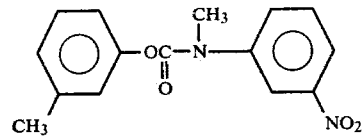

The following nitrourethanes (C) may be prepared analogously:

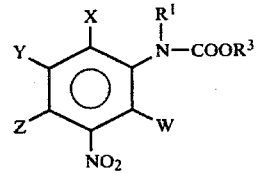

| W | X | Y | Z | R¹ | R³ | m.p. °C. |
|---|---|---|---|----|----|----------|
| H | H | H | H | H | 4-fluorophenyl | 116–167 |
| H | H | H | H | H | 1,4-dichlorophenyl | |
| H | H | H | H | H | methyl | 153–155 |
| H | CH₃ | H | H | H | methyl | 132–133 |
| H | H | H | H | benzyl | 4-chlorophenyl | |
| H | H | H | H | H | phenyl | 123–125 |
| H | H | H | H | H | 3-methoxyphenyl | |
| H | H | H | H | CH₃ | phenyl | 60–70 |
| H | H | H | H | H | 2-fluorophenyl | 145–146 |
| H | F | H | H | H | phenyl | 138–140 |
| H | H | H | H | H | 3-bromophenyl | 138 |
| H | H | H | H | CH₃OCH₂ | 3-methylphenyl | |
| H | H | H | H | H | 3,4-dimethylphenyl | 130–131 |
| H | H | CH₃ | H | H | methyl | 86–87 |
| H | H | H | H | H | 4-methoxyphenyl | 132–133 |
| H | CH₃ | H | H | H | ethyl | 131–133 |
| H | H | H | H | H | 3-fluorophenyl | 128–130 |
| H | H | H | H | H | ethyl | 64–66 |
| CH₃ | H | H | H | H | phenyl | 112–114 |
| H | H | H | H | H | 2-chloro-4-fluorophenyl | 146–147 |
| H | H | H | H | H | 2-chlorophenyl | 136–138 |
| H | F | H | F | H | methyl | |
| H | H | H | H | C₂H₅ | 4-cyanophenyl | |
| H | H | H | CH₃ | H | methyl | 114–117 |

-continued

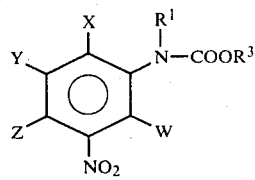

| W | X | Y | Z | R¹ | R³ | m.p. °C. |
|---|---|---|---|---|---|---|
| H | H | H | H | H | 3-trifluoromethylphenyl | 119-120 |
| Cl | H | Cl | H | CH₃ | 2-methoxyethyl | |
| H | H | H | H | H | 4-trifluoromethylphenyl | |
| H | H | H | H | CH₃ | cyclodecyl | |
| H | H | H | H | H | 4-ethylphenyl | 86-88 |
| H | H | H | Cl | H | phenyl | 125-127 |
| H | H | H | H | H | 3-chloro-4-fluorophenyl | |
| H | CH₃ | H | H | 4-methyl-benzyl | methyl | |
| H | H | H | H | H | 2,4,6-trimethylphenyl | 212-213 |
| H | H | H | Cl | H | methyl | 122-124 |
| H | H | H | H | H | 3,4-difluorophenyl | |
| H | NO₂ | H | H | C₂H₅ | 2,5-dichlorobenzyl | |
| H | H | H | H | H | 5-indanyl ( 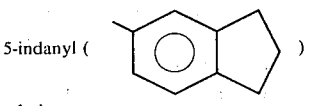 ) | 171-173 |
| H | H | H | CH₃ | H | ethyl | 80-81 |
| H | H | H | H | H | cyclododecyl | |
| H | H | H | H | H | 3-isopropylphenyl | 85-87 |
| H | H | H | H | C₂H₅OCH₂ | n-butyl | |
| H | H | H | H | H | 2-trifluoromethylphenyl | |
| H | H | H | H | H | cyclooctyl | 103-105 |
| H | H | H | H | H | 4-methylphenyl | 138-139 |
| H | H | H | H | H | 2,4-dibromophenyl | |
| H | H | H | H | H | tert.-butyl | 97-99 |
| H | H | H | H | H | 4-ethoxyphenyl | |
| H | H | H | H | H | 3-ethylphenyl | 85-86 |
| H | H | H | H | CH₃ | cycloheptyl | |
| H | H | H | H | H | 2,6-dimethylphenyl | 165-167 |
| H | H | CF₃ | H | H | isopropyl | 121-123 |
| H | F | H | H | H | 4-difluoromethoxyphenyl | |
| H | H | H | H | H | 3-methoxycarbonyl-aminophenyl | 172-174 |
| H | H | H | H | H | 2-methoxyphenyl | |
| H | H | H | H | H | tricyclo-[4,3,1²,⁵0¹,⁶]-decyl | 103-105 |
| H | H | H | H | H | 2-methylphenyl | 126-128 |
| H | H | H | H | H | 4-iodophenyl | |
| H | H | H | H | CH₃ | methyl | 54-56 |
| H | Cl | H | Cl | H | 2-cyclohexylphenyl | |
| H | H | H | H | H | 3-methyl-4-chlorophenyl | |
| H | H | H | H | H | 3,5-dimethylcyclohexyl | |
| H | H | H | H | H | 1-naphthyl | 141-142 |
| H | H | H | H | H | isopropyl | 86-88 |
| H | Br | H | H | H | ethyl | |
| H | H | H | H | H | 4-nitrophenyl | |
| H | F | H | H | H | methyl | 116-118 |
| CH₃ | H | H | H | benzyl | ethyl | |
| H | H | CF₃ | H | H | phenyl | 133-135 |
| H | H | H | Br | CH₃ | methyl | |
| H | H | H | H | H | 2,6-dimethylcyclohexyl | 121-123 |
| H | H | H | H | CH₃OCH₃— | 3-fluorophenyl | |
| H | OCH₃ | H | H | H | methyl | 131-132 |
| CH₃ | H | H | H | CH₃ | benzyl | |
| H | H | CF₃ | H | CH₃ | phenyl | |
| H | H | H | H | H | cycloheptyl | 102-104 |
| H | H | H | H | H | benzyl | 113-115 |
| H | NO₂ | H | CH₃ | H | methyl | |
| H | OCH₃ | H | H | H | phenyl | 209-211 |
| H | H | H | H | H | 3-methyl-5-isopropyl-phenyl | |
| H | H | H | H | benzyl | n-butyl | |
| H | H | H | H | H | norbornyl | 118-120 |
| H | H | H | H | H | 2-naphthyl | |
| H | H | NO₂ | H | C₂H₅ | 3-methylphenyl | |
| H | H | H | H | H | cyclopentyl | 110-112 |
| H | Cl | H | H | H | methyl | 136-138 |
| H | H | H | H | iso-propyl | 4-methylthiophenyl | |

-continued

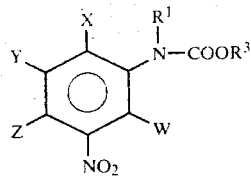

| W | X | Y | Z | R¹ | R³ | m.p. °C. |
|---|---|---|---|---|---|---|
| H | H | H | H | H | 3-methylcyclohexyl | 120–122 |
| H | H | H | H | H | cyclohexyl | 117–118 |
| H | H | H | H | H | 2-methylcyclohexyl | 100–102 |
| H | H | H | H | H | 1,3-dimethoxyisopropyl | 95–96 |
| H | H | H | H | H | 3(N,N-dimethylamino)-phenyl | 126–127 |
| H | H | H | H | H | 3,4-(tetramethylene)-phenyl | 164–166 |
| H | H | H | H | C₂H₅ | phenyl | 56–58 |
| H | H | H | H | H | hexahydrobenzyl | 127–128 |
| H | H | H | H | H | 3,3,5-trimethylcyclohexyl | 79–82 |
| H | H | H | H | H | 3-methyl-5-ethylphenyl | 115–117 |
| H | H | H | H | H | tert-amyl | 62–63 |
| H | H | H | H | H | 2,3,6-trimethylphenyl | 180–182 |
| H | H | H | H | H | 2,3,5,6-tetramethylphenyl | 237–238 |
| H | H | H | H | H | 4-tert-butylphenyl | 113–115 |
| H | H | H | H | H | 2,3,5-trimethylphenyl | 145–147 |
| H | H | H | H | H | 2-isopropyl-5-methylphenyl | 103–105 |
| H | H | H | H | H | 2-tert-butyl-4-methylphenyl | 154–156 |
| H | H | H | H | H | 2,6-dimethoxyphenyl | 155–157 |
| H | H | H | H | H | 3-methylphenyl | 106–108 |
| H | H | H | H | C₂H₅ | 3-methylphenyl | 75–77 |
| H | H | H | H | H | 2-methyl-6-isopropyl | 122–124 |
| H | H | H | H | H | 3,5-diethylphenyl | 128–130 |

II Aminourethanes

EXAMPLE C 3 parts of a hydrogenation catalyst (palladium on animal charcoal, 10%) was added to a solution of 135 parts by weight of 4-chlorophenyl N-(3-nitrophenyl)-carbamate in 900 parts by weight of tetrahydrofuran (absolute), and the mixture hydrogenated at room temperature and under a hydrogen pressure of 0.02 bar until the pressure no longer changes. The solution was freed from catalyst and dried with MgSO₄, and the solvent removed to such an extent that the crystalline reaction product was readily able to be suction filtered; m.p.: 186°–187° C.

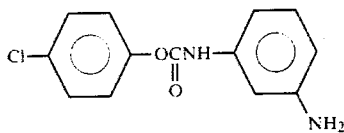

EXAMPLE D

While stirring vigorously, 25.2 parts by weight of phenyl chloroformate was very slowly dripped into a solution of 108 parts by weight of m-phenylene diamine in 1,000 parts by weight of water. After the reaction was over, the mixture was suction filtered, the solid washed several times with dilute hydrochloric acid, and the combined acidic solutions were neutralized with ammonia and suction filtered. The dry product thus obtained melts with decomposition at 178°–180° C. Structure:

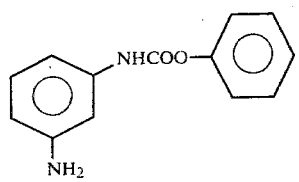

EXAMPLE E

While stirring vigorously, 130 parts by weight of 3-(O-phenylcarbamoyl)-nitrobenzene is added to a mixture, heated to 80° C., of 110 parts by weight of iron powder, 240 parts by weight of alcohol, 160 parts by weight of water and 7 parts by weight of concentrated hydrochloric acid in such portions that the temperature is kept at 80° C. without additional heating. The mixture is then refluxed for 1 hour and suction filtered while hot, the residue is digested with about 2,000 parts by weight of acetone, and twice the water is added to the combined filtrates before suction filtration is carried out; m.p. (after recrystallization from ethyl acetate): 180° C. (decomposes).

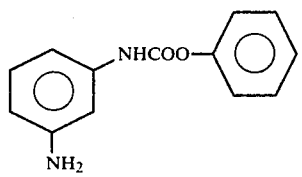

EXAMPLE F

While stirring vigorously, 52.1 parts by weight of phenyl chloroformate is dripped slowly into 51 parts by weight of 2,4-diaminonitrobenzene and 43 parts by weight of sodium bicarbonate in 600 parts by weight of tetrahydrofuran. The mixture is stirred for 14 hours and then filtered, and the residue is washed with tetrahydrofuran. The solution is freed from solvent to such a degree that the crystalline crude product is readily able to be suction filtered. After washing with diethyl ether and drying, the substance melts at 223°–225° C. According to the nmr spectrum and ultimate analysis, it has the following structure:

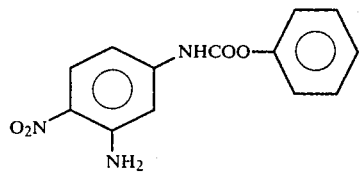

The following aminourethanes ($\underline{F}$) may be prepared analogously:

| W | X | Y | Z | $R^1$ | $R^3$ | m.p. °C. |
|---|---|---|---|---|---|---|
| H | H | H | H | H | 4-fluorophenyl | 166–167 |
| H | H | H | H | H | 2,4-dichlorophenyl | |
| H | H | H | H | H | methyl | 87–89 |
| H | CH$_3$ | H | H | H | methyl | not isolated |
| H | H | H | H | benzyl | 4-chlorophenyl | |
| H | H | H | NO$_2$ | H | methyl | 187–189 |
| H | H | H | H | H | 3-methoxyphenyl | |
| H | H | H | H | CH$_3$ | phenyl | 68–70 |
| H | H | H | H | H | 2-fluorophenyl | 172–173 |
| H | F | H | H | H | phenyl | not isolated |
| H | H | H | H | H | 3-bromophenyl | |
| H | H | H | H | CH$_3$OCH$_2$ | 3-methylphenyl | |
| H | H | CF$_3$ | H | H | methyl | not isolated |
| H | H | H | H | H | 3,4-dimethylphenyl | 155–157 |
| H | H | H | H | H | 4-methoxyphenyl | 146–149 |
| H | CH$_3$ | H | H | H | ethyl | not isolated |
| H | H | H | H | H | 3-fluorophenyl | decomposition |
| H | H | H | H | H | ethyl | not isolated |
| CH$_3$ | H | H | H | H | phenyl | 131–133 |
| H | H | H | H | H | 2-chloro-4-fluorophenyl | decomposition |
| H | H | H | H | H | 2-chlorophenyl | decomposition |
| H | F | H | F | H | methyl | not isolated |
| H | H | H | H | C$_2$H$_5$ | 4-Cyanophenyl | |
| H | H | H | CH$_3$ | H | methyl | not isolated |
| H | H | H | H | H | 3-trifluoromethylphenyl | 126–128 |
| Cl | H | Cl | H | CH$_3$ | 2-methoxyethyl | |
| H | H | H | H | H | 4-trifluoromethylphenyl | |
| H | H | H | H | CH$_3$ | cyclododecyl | |
| H | H | H | H | H | 4-ethylphenyl | 160–161 |
| H | H | H | Cl | H | phenyl | 215–217 |
| H | H | H | H | H | 3-chloro-4-fluorophenyl | |
| H | CH$_3$ | H | H | 4-methylbenzyl | methyl | |
| H | H | H | H | H | 2,4,6-trimethylphenyl | 150–152 |
| H | H | H | Cl | H | methyl | |
| H | H | H | H | H | 3,4-difluorophenyl | |
| H | NO$_2$ | H | H | C$_2$H$_5$ | 2,4-dichlorobenzyl | |

-continued

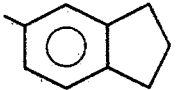

| W | X | Y | Z | R¹ | R³ | m.p. °C. |
|---|---|---|---|---|---|---|
| H | H | H | H | H | 5-indanyl | 184–186 |
| H | H | H | CH₃ | H | ethyl | not isolated |
| H | H | H | H | H | cyclododecyl | |
| H | H | H | H | H | 3-isopropylphenyl | 68–70 |
| H | H | H | H | C₂H₅OCH₂— | n-butyl | |
| H | H | H | H | H | 2-trifluoromethylphenyl | |
| H | H | H | H | H | cyclooctyl | 77–79 |
| H | H | H | H | H | 4-methylphenyl | 158–162 |
| H | H | H | H | H | 2,4-dibromophenyl | |
| H | H | H | H | H | tert-butyl | 109–110 |
| H | H | H | H | H | 4-ethoxyphenyl | |
| H | H | H | H | H | 3-ethylphenyl | 112–114 |
| H | H | H | H | CH₃ | cycloheptyl | |
| H | H | H | H | H | 2,6-dimethylphenyl | 160–161 |
| H | H | CF₃ | H | H | isopropyl | 102–104 |
| H | F | H | H | H | 4-difluoromethoxyphenyl | |
| H | H | H | H | H | 3(O-methylcarbamoyl)-phenyl | 149–151 |
| H | H | H | H | H | 2-methoxyphenyl | |
| H | H | H | H | H | tricyclo-[4,3,1²,⁵0¹,⁶]-decyl | 130–131 |
| H | H | H | H | H | 2-methylphenyl | 170–172 |
| H | H | H | H | H | 4-iodophenyl | |
| H | H | H | H | CH₃ | methyl | not isolated |
| H | Cl | H | Cl | H | 2-cyclohexylphenyl | |
| H | H | H | H | H | 3-methyl-4-chlorophenyl | |
| H | H | H | H | H | 3,5-dimethylcyclohexyl | |
| H | H | H | H | H | 1-naphthyl | 146–148 |
| H | H | H | H | H | isopropyl | 66–68 |
| H | Br | H | H | H | ethyl | |
| H | H | H | H | H | 4-nitrophenyl | |
| H | F | H | H | H | methyl | not isolated |
| CH₃ | H | H | H | benzyl | ethyl | |
| H | H | CF₃ | H | H | phenyl | 214–216 |
| H | H | H | Br | CH₃ | methyl | |
| H | H | H | H | H | 2,6-dimethylcyclohexyl | not isolated |
| H | H | H | H | CH₃OCH₂— | 3-fluorophenyl | |
| H | OCH₃ | H | H | H | methyl | not isolated |
| CH₃ | H | H | H | CH₃ | benzyl | |
| H | H | CF₃ | H | CH₃ | phenyl | |
| H | H | H | H | H | cycloheptyl | 86–88 |
| H | H | H | H | H | benzyl | not isolated |
| H | NO₂ | H | CH₃ | H | methyl | |
| H | OCH₃ | H | H | H | phenyl | 84–86 |
| H | H | H | H | H | 3-methyl-5-isopropyl-phenyl | not isolated |
| H | H | H | H | benzyl | n-butyl | |
| H | H | H | H | H | nornornyl | 150–151 |
| H | H | H | H | H | 2-naphthyl | |
| H | H | NO₂ | H | C₂H₅ | 3-methylphenyl | |
| H | H | H | H | H | cyclopentyl | not isolated |
| H | Cl | H | H | H | methyl | not isolated |
| H | H | H | H | iso-propyl | 4-methylthiophenyl | |
| H | H | H | H | H | 3-methylcyclohexyl | 95–97 |
| H | H | H | H | CH₃ | 3-methylphenyl | 114–115 |
| H | H | H | H | C₂H₅ | phenyl | 104–106 |
| H | H | H | H | C₂H₅ | 3-methylphenyl | 104–105 |
| H | H | H | H | H | 2-isopropyl-5-methyl-phenyl | 122–123 |

-continued

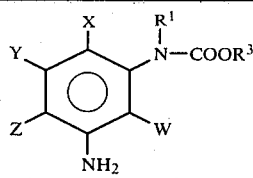

| W | X | Y | Z | R¹ | R³ | m.p. °C. |
|---|---|---|---|----|----|----------|
| H | H | H | H | H | 3-methylphenyl | 142–144 |
| H | H | H | H | H | 2-tert-butyl-4-methyl-phenyl | 89–91 |
| H | H | H | H | H | tert-amyl | 65–67 |
| H | H | H | H | H | hexahydrobenzyl | 106–108 |
| H | H | H | H | H | 3,4-(tetramethylene)-phenyl | 181–183 |
| H | H | H | H | H | 3-methyl-5-ethylphenyl | 102–104 |
| H | H | H | H | H | 4-tert-butylphenyl | 175–177 |
| H | H | H | H | H | 2,3,5-trimethylphenyl | 152–154 |
| H | H | H | H | H | 2,3,6-trimethylphenyl | 155–156 |
| H | H | H | H | H | 3-(N,N-dimethylamine)-phenyl | 132–133 |
| H | H | H | H | H | 3,5-diethylphenyl | 121–123 |
| H | H | H | H | H | 3,3,5-trimethylcyclohexyl | 98–100 |
| H | H | H | H | H | cyclohexyl | 122–124 |
| H | H | H | H | H | 2-methylcyclohexyl | |
| H | H | H | H | H | 1,3-dimethoxyisopropyl | |
| H | H | H | H | H | 2-methyl-6-isopropyl-phenyl | 133–135 |

Note:
The amines termed "not isolated" were further reacted direct after catalytic reduction without isolation and purification.

III Diurethanes

EXAMPLE 1

11 parts by weight of sodium bicarbonate was added to a solution of 18.7 parts by weight of 4-chlorophenyl N-(3-aminophenyl)-carbamate in 125 parts by weight of tetrahydrofuran (absolute); subsequently, 9.4 parts by weight of methyl chloroformate was metered in at 20° to 25° C. and while cooling. To complete the reaction, the mixture was stirred for 1 hour at room temperature, after which it was filtered and the residue was concentrated in vacuo. The oily residue was dissolved in a small amount of ether and crystallized by adding petroleum ether; m.p.: 166°–167° C. (No. 1).

The compound has the following structural formula:

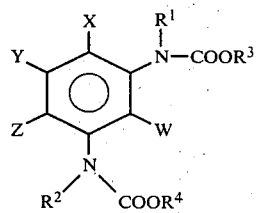

The following compounds were prepared analogously;

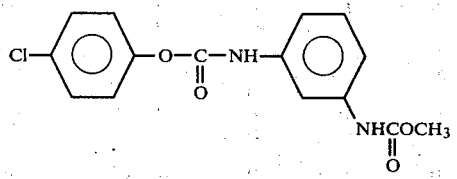

| No. | W | X | Y | Z | R¹ | R² | R³ | R⁴ | m.p. °C. |
|-----|---|---|---|---|----|----|----|----|----------|
| 2 | H | H | H | H | H | H | phenyl | methyl | 162–164 |
| 3 | H | Cl | H | H | H | H | methyl | phenyl | 133–135 |
| 4 | H | H | H | H | H | H | 2-fluorophenyl | ethyl | 120–121 |
| 5 | CH₃ | H | H | H | H | H | ethyl | phenyl | 181–183 |
| 6 | H | H | H | H | H | H | methyl | 3-fluorophenyl | 138–139 |
| 7 | H | H | H | H | CH₃ | H | phenyl | methyl | 142–143 |
| 8 | H | H | H | H | H | H | 4-fluorophenyl | methyl | 154–155 |
| 9 | H | H | H | Cl | H | H | phenyl | ethyl | 147–149 |
| 10 | H | H | H | H | H | CH₃ | ethyl | phenyl | 150–152 |
| 11 | H | H | H | H | H | H | ethyl | 4-ethylphenyl | 94–96 |
| 12 | H | H | H | H | H | H | 2,6-dimethyl-cyclohexyl | allyl | 100–103 |
| 13 | H | H | H | H | CH₃ | H | 3-methylphenyl | methyl | 103–104 |
| 14 | H | H | H | H | H | H | 3-methoxycarbo- | methyl | 188–190 |

-continued

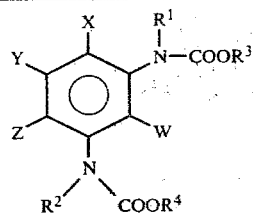

| No. | W | X | Y | Z | R¹ | R² | R³ | R⁴ | m.p. °C |
|---|---|---|---|---|---|---|---|---|---|
| | | | | | | | nylaminophenyl | | |
| 15 | H | H | H | H | H | H | isobutyl | phenyl | 137–140 |
| 16 | H | Cl | H | H | H | H | methyl | 3-methylphenyl | 154–156 |
| 17 | H | H | H | H | H | H | ethyl | 2,4-dichlorophenyl | |
| 18 | H | H | H | H | H | H | 2-fluorophenyl | methyl | 176–177 |
| 19 | H | H | H | H | benzyl | H | methyl | 4-chlorophenyl | |
| 20 | CH₃ | H | H | H | H | H | phenyl | methyl | 164–166 |
| 21 | H | H | H | H | H | H | methyl | 3-methoxyphenyl | |
| 22 | H | H | H | H | H | H | ethyl | 3-fluorophenyl | 131–132 |
| 23 | H | H | H | H | H | H | phenyl | ethyl | 152–153 |
| 24 | H | H | H | H | H | H | 3-bromophenyl | methyl | 168–170 |
| 25 | H | H | H | H | H | CH₃OCH₂— | methyl | 3-methylphenyl | |
| 26 | H | H | H | H | H | H | 4-fluorophenyl | phenyl | 161–164 |
| 27 | H | H | H | H | H | H | 2,4-dichlorophenyl | methyl | 152–154 |
| 28 | H | H | H | H | CH₃ | H | methyl | phenyl | oil |
| 29 | H | H | H | H | H | H | 4-methoxyphenyl | methyl | 165–166 |
| 30 | H | H | H | H | H | H | methyl | 3-ethylphenyl | 106–107 |
| 31 | H | H | H | H | H | H | 3-methoxyphenyl | ethyl | |
| 32 | H | H | H | H | H | H | phenyl | 2-chloroethyl | 118–120 |
| 33 | H | H | H | H | H | H | ethyl | 4-methoxyphenyl | 142–143 |
| 34 | H | H | H | H | H | H | methyl | 3-(N,N-dimethyl-amino)-phenyl | 169–171 |
| 35 | H | H | H | H | H | H | 4-fluorophenyl | ethyl | 129–132 |
| 36 | H | H | H | H | H | H | 5-indanyl | ethyl | 101–103 |
| 37 | H | H | H | H | H | H | 2-chlorophenyl | methyl | 170–171 |
| 38 | H | H | H | H | C₂H₅ | H | 4-cyanophenyl | methyl | |
| 39 | H | H | H | H | H | H | cyclopentyl | phenyl | 158–160 |
| 40 | Cl | H | Cl | H | CH₃ | H | 2-methoxyethyl | 1-naphthyl | |
| 41 | H | H | H | H | H | H | methyl | 4-trifluoromethyl-phenyl | |
| 42 | H | H | H | H | H | H | 2-methoxyethyl | 4-fluorophenyl | 95–97 |
| 43 | H | H | H | H | H | CH₃ | methyl | cyclododecyl | |
| 44 | H | H | H | H | H | H | phenyl | isopropyl | 114–115 |
| 45 | H | H | H | H | H | H | ethyl | 2-chlorophenyl | 134–135 |
| 46 | H | H | H | H | H | H | 4-methylphenyl | ethyl | 110–112 |
| 47 | H | H | H | H | H | H | 3-(N,N-dimethyl-amino)-phenyl | ethyl | |
| 48 | H | H | H | H | H | H | ethyl | 3-bromophenyl | |
| 49 | H | H | H | H | H | H | 3-chloro-4-fluoro-phenyl | methyl | |
| 50 | H | H | H | H | H | H | ethyl | 4-chlorophenyl | 146–148 |
| 51 | H | H | H | H | H | H | 4-trifluoromethyl-phenyl | ethyl | |
| 52 | H | CH₃ | H | H | H | 4-methyl-benzyl | phenyl | methyl | |
| 53 | H | H | H | Cl | H | H | methyl | 4-methylthiophenyl | |
| 54 | H | H | H | H | H | H | 3-trifluoromethyl-phenyl | ethyl | 113–115 |
| 55 | H | H | H | H | H | H | methyl | 4-methylphenyl | 187–189 |
| 56 | H | H | H | H | H | H | 3,4-difluorophenyl | ethyl | |
| 57 | H | NO₂ | H | H | C₂H₅ | H | 2,4-dichlorobenzyl | methyl | |
| 58 | H | H | H | H | H | H | methyl | cyclododecyl | 123–125 |
| 59 | H | H | H | H | H | H | 3-isopropylphenyl | ethyl | 59–61 |
| 60 | H | H | H | H | H | H | 5-indanyl | methyl | 152–154 |
| 61 | H | H | H | H | H | C₂H₅OCH₂— | methyl | n-butyl | |
| 62 | H | H | H | H | H | H | cyclododecyl | phenyl | |
| 63 | H | H | H | H | H | H | 3-trifluoromethyl-phenyl | methyl | 137–139 |
| 64 | H | H | H | H | H | H | cyclooctyl | ethyl | |
| 65 | H | H | H | H | H | H | methyl | 3,4-difluorophenyl | |
| 66 | H | H | H | H | H | H | methyl | 3-isopropylphenyl | 61–63 |
| 67 | H | H | H | H | H | H | phenyl | cyclooctyl | |
| 68 | H | H | H | H | H | H | ethyl | 3-ethylphenyl | oil |
| 69 | H | H | H | H | H | H | 3-chloro-4-fluoro-phenyl | ethyl | |
| 70 | H | H | H | H | H | H | methyl | 2,4-dibromophenyl | |
| 71 | H | H | H | H | H | H | cyclopentyl | methyl | 104–106 |
| 72 | H | H | H | H | H | H | ethyl | cyclododecyl | |
| 73 | H | H | H | H | H | H | methyl | cyclooctyl | oil |
| 74 | H | H | H | H | H | H | 3,4-dimethylphenyl | methyl | 94–96 |

-continued

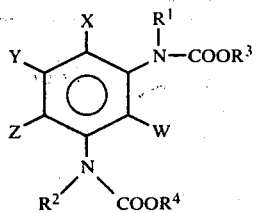

| No. | W | X | Y | Z | R¹ | R² | R³ | R⁴ | m.p. °C. |
|---|---|---|---|---|---|---|---|---|---|
| 75 | H | OCH₃ | H | H | H | H | methyl | phenyl | 139–140 |
| 76 | H | H | H | H | H | H | 2-chloro-4-fluoro-phenyl | ethyl | 130–132 |
| 77 | H | H | H | H | H | H | methyl | 2,6-dimethylcyclo-hexyl | 110–112 |
| 78 | H | H | H | H | H | H | ethyl | 2,4-dibromophenyl | |
| 79 | H | H | H | H | H | H | ethyl | 3,4-dimethylphenyl | 152–154 |
| 80 | H | H | H | H | H | H | 2-trifluoromethyl-phenyl | methyl | |
| 81 | H | H | H | H | H | H | 4-nitrophenyl | methyl | |
| 82 | H | H | H | H | H | H | cycloheptyl | methyl | 117–119 |
| 83 | H | H | H | NO₂ | H | H | methyl | phenyl | 153–155 |
| 84 | H | H | H | H | H | H | 4-ethoxyphenyl | ethyl | |
| 85 | H | H | H | H | H | H | tert-butyl | methyl | 116–118 |
| 86 | H | H | H | H | CH₃ | H | cycloheptyl | propargyl | |
| 87 | H | H | H | H | H | H | methyl | 2-chloro-4-fluoro-phenyl | 170–172 |
| 88 | H | H | H | H | H | H | ethyl | 2-trifluoromethyl-phenyl | |
| 89 | H | H | H | H | H | H | methyl | 4-ethoxyphenyl | |
| 90 | H | H | H | H | H | H | norbornyl | methyl | 110–112 |
| 91 | H | H | H | H | H | H | ethyl | 2,6-dimethylphenyl | 118–120 |
| 92 | H | H | H | H | H | H | 2,4,6-trimethyl-phenyl | methyl | 158–159 |
| 93 | H | H | H | NO₂ | H | H | phenyl | methyl | 213–215 |
| 94 | H | H | H | H | H | H | methyl | 2,6-dimethylphenyl | 133–134 |
| 95 | H | H | H | H | H | H | 4-ethylphenyl | methyl | 148–150 |
| 96 | H | F | H | H | H | H | 4-difluoromethoxy-phenyl | methyl | |
| 97 | H | H | H | H | H | H | benzyl | phenyl | 140–142 |
| 98 | H | H | H | H | H | H | methyl | 2-methoxyphenyl | 155–157 |
| 99 | H | H | H | H | H | H | phenyl | tert-butyl | 158–160 |
| 100 | H | H | H | H | H | H | tricyclo-[4,3,1²,⁵0¹,⁶]-decyl | methyl | |
| 101 | H | H | H | H | H | H | 2-methylphenyl | ethyl | 114–115 |
| 102 | H | H | H | H | H | H | ethyl | 2,4,6-trimethyl-phenyl | 120–124 |
| 103 | H | H | H | NO₂ | H | H | n-butyl | methyl | |
| 104 | H | H | H | H | H | H | ethyl | tricyclo-[4,3,1²,⁵0¹,⁶]-decyl | |
| 105 | H | H | H | H | H | H | methyl | benzyl | 108–110 |
| 106 | H | H | H | H | H | H | methyl | 4-iodophenyl | |
| 107 | H | H | H | H | H | H | 2-methylphenyl | methyl | 158–159 |
| 108 | H | H | H | H | CH₃ | H | ethyl | 3-methylphenyl | 101–102 |
| 109 | H | H | H | H | H | H | 2-methoxyphenyl | ethyl | |
| 110 | H | H | H | H | H | H | tricyclo-[4,3,1²,⁵0¹,⁶]-decyl | phenyl | |
| 111 | H | H | H | H | H | H | norbornyl | phenyl | 190–192 |
| 112 | H | H | H | H | H | H | ethyl | 4-iodophenyl | |
| 113 | H | Cl | H | Cl | H | CH₃ | 2-cyclohexylphenyl | methyl | |
| 114 | H | H | H | H | H | H | phenyl | n-propyl | 159–161 |
| 115 | H | H | H | H | H | H | methyl | 3-methyl-4-chloro-phenyl | 160–162 |
| 116 | H | F | H | F | H | H | phenyl | methyl | 164–166 |
| 117 | H | H | H | H | H | H | 3,5-dimethylcyclo-hexyl | ethyl | |
| 118 | H | H | H | F | H | H | phenyl | methyl | 119–122 |
| 119 | H | H | H | H | H | H | propargyl | phenyl | 92–94 |
| 120 | H | H | H | H | H | H | methyl | 1-naphthyl | 174–175 |
| 121 | H | Br | H | H | H | ClCH₂— | ethyl | phenyl | |
| 122 | H | H | H | H | H | H | 3-methyl-5-iso-propylphenyl | methyl | 63–65 |
| 123 | H | H | H | H | H | H | methyl | 3,5-dimethylcyclo-hexyl | 112–119 |
| 124 | H | H | H | CH₃ | H | H | methyl | cyclohexyl | 146–148 |
| 125 | H | H | H | H | H | H | 3-methyl-4-chloro-phenyl | ethyl | |

-continued

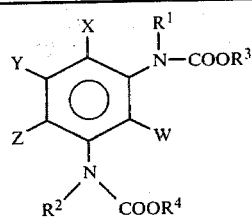

| No. | W | X | Y | Z | R¹ | R² | R³ | R⁴ | m.p. °C. |
|---|---|---|---|---|---|---|---|---|---|
| 126 | CH₃ | H | H | H | benzyl | H | ethyl | cyclohexyl | |
| 127 | H | H | H | H | H | H | phenyl | allyl | 90–93 |
| 128 | H | H | H | H | H | H | 2-naphthyl | methyl | |
| 129 | H | H | H | Br | CH₃ | H | methyl | 4-chlorobutyn-2-yl-1 | |
| 130 | H | F | H | H | H | H | phenyl | methyl | 133–135 |
| 131 | H | H | H | H | CH₃OCH₂— | H | 3-fluorophenyl | methyl | |
| 132 | H | H | H | H | H | H | ethyl | 3-chlorophenyl | 109–112 |
| 133 | H | H | H | F | H | H | ethyl | phenyl | 163–165 |
| 134 | H | H | H | H | H | H | 3,5-dimethylcyclohexyl | phenyl | |
| 135 | H | H | CF₃ | H | H | CH₃ | methyl | phenyl | |
| 136 | H | NO₂ | H | CH₃ | H | H | methyl | 4-fluorophenyl | |
| 137 | CH₃ | H | H | H | CH₃ | H | benzyl | propargyl | |
| 138 | H | H | H | H | H | H | phenyl | butyn-1-yl-3 | 117–119 |
| 139 | H | H | H | H | CH₃ | H | 3-methyl-5-isopropylphenyl | methyl | |
| 140 | H | CH₃ | H | H | H | H | 3-methylphenyl | methyl | 155–157 |
| 141 | H | H | H | H | H | benzyl | sec-butyl | n-butyl | |
| 142 | H | H | NO₂ | H | C₂H₅ | H | 3-methylphenyl | allyl | |
| 143 | H | H | H | CH₃ | H | H | methyl | 3-chlorophenyl | 168–170 |
| 144 | H | H | H | H | H | H | isopropyl | 3-methylphenyl | oil |
| 145 | H | H | H | H | isopropyl | H | 4-methylthiophenyl | n-propyl | |
| 146 | H | F | H | F | H | H | 3-thiocyanatophenyl | methyl | |
| 147 | H | H | H | H | H | H | sec-butyl | phenyl | 117–119 |
| 148 | H | H | H | H | H | H | methyl | 3-aminophenyl | |
| 149 | H | CH₃ | H | H | H | H | methyl | 3-chlorophenyl | 105–107 |
| 150 | H | H | H | H | H | H | diphenyl | methyl | |
| 151 | H | H | H | H | H | H | 3(N',N'-dimethylureido)-phenyl | allyl | |
| 152 | H | CH₃ | H | H | H | H | methyl | phenyl | 147–149 |
| 153 | H | F | H | F | H | CH₃ | methyl | 3-phenoxyphenyl | |
| 154 | H | H | H | CH₃ | H | H | isopropyl | methyl | 118–120 |
| 155 | H | H | H | H | H | H | phenyl | n-butyl | 108–110 |
| 156 | H | CH₃ | H | H | H | H | ethyl | phenyl | 170–172 |
| 157 | H | H | H | H | H | H | 3-methoxycarbonylphenyl | methyl | |
| 158 | H | H | H | H | H | H | methyl | n-decyl | 85–87 |
| 159 | H | CH₃ | H | H | H | H | phenyl | ethyl | 146–148 |
| 160 | H | H | H | H | H | H | 4-phenoxyphenyl | ethyl | |
| 161 | CH₃ | H | CH₃ | H | H | H | propargyl | (3-acetylamino)-phenyl | |
| 162 | H | H | H | H | H | H | phenyl | n-decyl | 83–86 |
| 163 | H | H | CF₃ | H | H | H | ethyl | phenyl | 66–68 |
| 164 | H | H | H | H | H | H | 2-methoxyethyl | phenyl | oil |
| 165 | H | H | H | H | H | H | methyl | 4(CH₃SO₂—)-phenyl | |
| 166 | H | H | H | H | H | H | 3(CH₃SO₃)-phenyl | ethyl | |
| 167 | H | H | CF₃ | H | H | H | methyl | phenyl | 74–76 |
| 168 | H | H | H | H | H | H | isopropyl | 3-chlorophenyl | 103–105 |
| 169 | H | H | H | H | H | H | 4-tert-butylcyclohexyl | phenyl | 161–163 |
| 170 | H | H | H | H | H | H | phenyl | phenyl | 175–176 |
| 171 | H | H | H | H | H | H | ethyl | 3-methylphenyl | 76–78 |
| 172 | H | H | H | H | H | H | methyl | 4-tert-butylcyclohexyl | oil |
| 173 | H | H | CF₃ | H | H | H | 3-methylphenyl | methyl | 60–63 |
| 174 | H | H | H | H | H | H | methyl | 3-chlorophenyl | 155–158 |
| 175 | H | H | H | H | H | H | phenyl | 2-ethyl-n-hexyl | oil |
| 176 | H | H | H | H | H | H | cyclohexyl | phenyl | 189–190 |
| 177 | H | OCH₃ | H | H | H | H | phenyl | methyl | 171–173 |
| 178 | H | Cl | H | NO₂ | H | H | 3-acetylphenyl | propargyl | |
| 179 | H | H | H | H | H | H | 2-ethyl-n-hexyl | methyl | oil |
| 180 | H | H | H | OCH₃ | H | H | phenyl | ethyl | 146–148 |
| 181 | H | H | H | H | H | H | methyl | 3-methylphenyl | 137–139 |
| 182 | H | H | H | H | H | H | 4(CH₃)₂NSO₂)-phenyl | methyl | |
| 183 | H | H | H | H | H | H | 3-methylcyclohexyl | methyl | 137–139 |
| 184 | H | H | H | H | H | H | cyclohexyl | methyl | 128–130 |
| 185 | H | H | H | H | H | H | methyl | propargyl | 84–86 |
| 186 | H | H | CF₃ | H | H | H | phenyl | isopropyl | 75–77 |

-continued

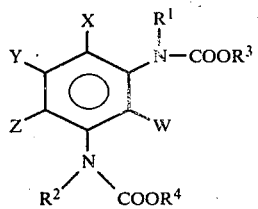

| No. | W | X | Y | Z | R¹ | R² | R³ | R⁴ | m.p. °C. |
|---|---|---|---|---|---|---|---|---|---|
| 187 | H | H | H | H | H | H | methyl | 3-(1'-ethoxycarbonylethoxy)-phenyl | |
| 188 | H | H | H | CH₃ | H | H | 2-chloropropen-(1)-yl-(3) | 2-chloropropen-(1)-yl-(3) | 103–104 |
| 189 | H | H | H | H | ethyl | H | methyl | phenyl | |
| 190 | H | CH₃ | H | H | H | H | 1-chlorobutyn-(2)-yl-(4) | 1-chlorobutyn-(2)-yl-(4) | 117–118 |
| 191 | H | H | H | H | H | benzyl | phenyl | methyl | |
| 192 | H | H | H | H | CH₃ | H | methyl | 4-fluorophenyl | |
| 193 | H | H | H | H | H | H | methyl | methyl | 161–163 |
| 194 | H | H | H | H | H | H | n-butyl | methyl | 70–72 |
| 195 | H | H | NO₂ | H | H | CH₃ | allyl | 4-benzoylphenyl | |
| 196 | H | H | H | H | H | H | methyl | methoxyethyl | 76–79 |
| 197 | H | H | H | H | H | H | 1-naphthyl | ethyl | 120–121 |
| 198 | H | H | H | H | H | H | methyl | ethyl | 116–118 |
| 199 | H | H | H | H | H | C₂H₅ | methyl | 3-methylphenyl | 107–109 |
| 200 | H | H | H | H | H | H | isopropyl | methyl | 110–112 |
| 201 | H | H | H | H | H | H | 3-methyl-5-ethyl-phenyl | methyl | 114–116 |
| 202 | H | H | H | H | C₂H₅ | H | phenyl | methyl | 133–135 |
| 203 | H | H | H | H | H | H | ethyl | 3-methyl-5-ethyl-phenyl | 87–89 |
| 204 | H | H | H | H | H | H | 3,3,5-trimethyl-cyclohexyl | methyl | 64–67 |
| 205 | H | H | H | H | H | H | 3,4-(tetramethylenephenyl) | methyl | 149–151 |
| 206 | H | H | H | H | H | H | ethyl | norbornyl | 86–88 |
| 207 | H | H | H | H | CH₃ | H | 4-chlorophenyl | methyl | 183–185 |
| 208 | H | H | H | H | H | H | 2-methyl-6-isopropylphenyl | methyl | 127–129 |
| 209 | H | H | H | H | H | H | 3-methylcyclohexyl | ethyl | oil |
| 210 | H | H | H | H | H | H | 3,5-diethylphenyl | methyl | 113–115 |
| 211 | H | H | H | H | H | H | 2-isopropyl-5-methylphenyl | methyl | 142–144 |
| 212 | H | H | H | H | H | H | ethyl | 3,4-(tetramethylene)-phenyl | 91–93 |
| 213 | H | H | H | H | H | H | methyl | 2-tert-butyl-4-methylphenyl | 166–168 |
| 214 | H | H | H | H | H | H | tert-amyl | methyl | 152–154 |
| 215 | H | H | H | H | H | H | methyl | hexahydrobenzyl | 85–86 |
| 216 | H | H | H | H | H | H | tert-butyl | ethyl | 98–100 |
| 217 | H | H | H | H | H | H | ethyl | isopropyl | 117–119 |
| 218 | H | H | H | H | H | H | cyclohexyl | ethyl | oil |
| 219 | H | H | H | H | H | H | ethyl | 2,6-dimethylcyclohexyl | oil |
| 220 | H | H | H | H | H | H | 4-tert-butylphenyl | methyl | 120–121 |
| 221 | H | H | H | H | H | H | methyl | 2,3,6-trimethylphenyl | 167–169 |
| 222 | H | H | H | H | H | H | sec-butyl | methyl | 92–94 |
| 223 | H | H | H | H | H | H | 2,3,5-trimethylphenyl | methyl | 165–167 |
| 224 | H | H | H | H | CH₃ | H | methyl | methyl | 62–63 |
| 225 | H | H | H | H | H | CH₃ | methyl | 2,4,6-trimethylphenyl | 135–137 |
| 226 | H | H | H | H | H | H | methyl | butyn-1-yl-3 | 109–111 |
| 227 | H | H | H | H | H | H | 2,6-dimethoxyphenyl | methyl | |
| 228 | H | H | H | H | H | H | methyl | 2,3,5,6-tetramethylphenyl | 214–216 |
| 229 | H | H | H | H | H | H | CH₃ | ![structure with OCH₃, OCH₃] | 105–107 |
| 230 | H | H | H | H | H | H | CH₃ | 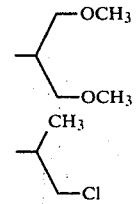 | oil |

-continued
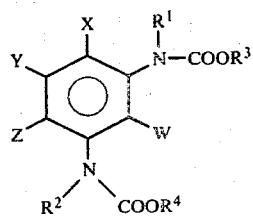
| No. | W | X | Y | Z | R¹ | R² | R³ | R⁴ | m.p. °C. |
|---|---|---|---|---|---|---|---|---|---|
| 231 | H | H | H | H | H | H | CH₃ | -CH₂-CH(OCH₃)-CH₂Cl | |
| 232 | H | H | H | H | H | H | CH₃ | -C(CH₃)₂-CH₂Cl | 84–86 |
| 233 | H | H | H | H | H | H | -CH₂-C(CH₃)₃ | CH₂-C≡CH | 111–113 |
| 234 | H | H | H | H | H | H | -C(CH₃)₂-CH₃ | -CH(CH₃)₂ | 131–133 |
| 235 | H | H | H | H | H | H | -C(CH₃)₃ | CH₂-CH=CH₂ | 95–97 |
| 236 | H | H | H | H | H | H | C₆H₅ | -CH₂-CH(OCH₃)-CH₂OCH₃ | oil |
| 237 | H | H | H | H | CH₃ | H | C₆H₅ | -C(CH₃)₃ | 134–136 |
| 238 | H | H | H | H | C₂H₅ | H | C₆H₅ | C₂H₅ | 135–137 |
| 239 | H | H | H | H | H | H | 4-F-C₆H₄ | -C(CH₃)₃ | 128–30 |
| 240 | H | H | H | H | H | H | 4-Cl-C₆H₄ | -C(CH₃)₃ | 163–165 |
| 241 | H | H | H | H | H | H | 4-Br-C₆H₄ | CH₃ | 168–170 |
| 242 | H | H | H | H | H | H | 2,3-Cl₂-C₆H₃ | CH₃ | 167–168 |
| 243 | H | H | H | H | H | H | 2,5-(CH₃)₂-4-Cl-C₆H₂ | CH₃ | 162–164 |

-continued
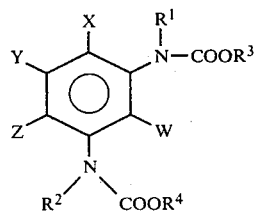
| No. | W | X | Y | Z | R¹ | R² | R³ | R⁴ | m.p. °C. |
|---|---|---|---|---|---|---|---|---|---|
| 244 | H | H | H | H | H | H | 4-methyl-2-nitrophenyl | CH₃ | 138–140 |
| 245 | H | H | H | H | H | H | 4-methyl-2-methoxyphenyl | CH₃ | 131–133 |
| 246 | H | H | H | H | H | H | 2,3,4-trimethoxyphenyl | CH₃ | 115–118 |
| 247 | H | H | H | H | H | H | 2-ethylphenyl | CH₃ | 137–139 |
| 248 | H | H | H | H | H | H | 2-isopropylphenyl | CH₃ | 118–120 |
| 249 | H | H | H | H | H | H | 4-isopropylphenyl | CH₃ | 152–154 |
| 250 | H | H | H | H | H | H | 2,3-dimethylphenyl | CH₃ | 179–181 |
| 251 | H | H | H | H | H | H | 2,4-dimethylphenyl | CH₃ | 130–132 |
| 252 | H | H | H | H | H | H | 2-methyl-4-isopropylphenyl | CH₃ | 117–119 |

-continued

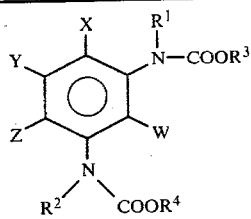

| No. | W | X | Y | Z | R¹ | R² | R³ | R⁴ | m.p. °C |
|---|---|---|---|---|---|---|---|---|---|
| 253 | H | H | H | H | H | H | 2-CH₃-6-iso-C₃H₇-phenyl | CH₃ | 127–129 |
| 254 | H | H | H | H | H | H | 2-CH₃-6-iso-C₃H₇-phenyl | C₂H₅ | 70–72 |
| 255 | H | H | H | H | H | H | 3,5-di-tert-C₄H₉-phenyl | CH₃ | 151–152 |
| 256 | H | H | H | H | H | H | 1-methylcyclopentyl | CH₃ | 145–147 |
| 257 | H | H | H | H | H | H | 2-methylcyclohexyl | CH₃ | oil |
| 258 | H | H | H | H | H | H | 4-methylcyclohexyl | CH₃ | 74–76 |
| 259 | H | H | H | H | H | H | 4-(H₃COOC—HN)-phenyl | CH₃ | 212–214 |

The herbicidal properties of some of the new compounds were examined under controlled conditions and in the open.

Greenhouse experiments

Plastic flowerpots having a volume of 300 cm³ were filled with a sandy loam. Seeds were then sown, or vegetatively reproduced species transplanted. The test plants were separated according to species. The active ingredients were suspended or emulsified in water as the vehicle and sprayed onto the surface of the soil by means of atomizing nozzles. After treatment, the vessels were lightly sprinkler-irrigated and then covered with transparent plastic hoods until the plants had taken root. For the postemergence (leaf) treatment, the plants were first grown to a height of from 3 to 10 cm, depending on habit, before being treated. The pots were of course not irrigated, and no hoods were placed on the pots. The plants were placed in either cooler or warmer parts of the greenhouse, depending on their temperature requirements. The experiments were run for from 2 to 4 weeks. During this period the plants were tended and their reaction to the individual treatments was assessed. The application rate of the compounds examined is given in kg/ha of active ingredient. For assessment, the 0 to 100 scale was used, 0 denoting no damage or normal emergence, and 100 denoting no emergence or complete destruction.

Experiments in climatic cabinets

Experiments were carried out in climatic cabinets of 1,000 liters volume, with selected agents and sugarbeets and mustard as test plants. The intensity of illumination was 10,000 lux, and the illumination duration 16 hours per day. The relative humidity was adjusted to 80%. Temperature ranges of 12° C. and 22° C. were kept separately so as to be able to ascertain the influence of temperature on the action of the agents.

The test plants were initially grown in the abovementioned pots in the greenhouse until 1 to 2 genuine leaves had developed. The plants were then treated as in the greenhouse experiments and transferred to the climatic cabinets. The observation periods lasted 3 weeks. The 0 to 100 scale was again employed for assessment.

Experiments in the open

Postemergence treatments were carried out on small plots. The compounds were applied, as an emulsion or suspension in water, with the aid of a motor-driven plot spray mounted on a hitch. All the experiments were observed for several weeks and again assessed on the 0 to 100 scale.

Results

The experiment carried out in accordance with the above methods gave the following results. The individual figures are contained in Tables 2 to 14.

1. In addition to a pronounced herbicidal action when applied to leaves, some of the new compounds had a noteworthy herbicidal effect when applied before the test plants had emerged (Tables 2, 11).
2. The herbicidal action on postemergence application was observed in numerous experiments with widely varying plant species from the most different botanical families (Tables 2 to 14). Prior art active ingredients gave in general poorer results than, and in some cases similar results to, the new active ingredients.
3. Numerous agricultural and horticultural crop plants suffered no appreciable damage, if any at all, after treatment with the new compounds (Tables 4, 5, 6, 7, 8, 9, 10, 12, 13); they may therefore be employed as selective herbicidal agents for controlling unwanted plant growth in a number of crop plants. Representatives of the new active ingredients are excellently suited for controlling weeds in soybeans (Table 12). Generally, the new compounds offered clear advantages over the prior art compounds in a wide variety of crops.

Table 1

| Botanical name | Abbreviation in tables | Common name |
|---|---|---|
| Alopecurus myosuroides | Alopec. myos. | slender foxtail (blackgrass) |
| Amaranthus retroflexus | Amar. ret. | redroot pigweed |
| Anthemis spp. | Anth. | chamomile |

Table 1-continued

| Botanical name | Abbreviation in tables | Common name |
|---|---|---|
| Arachis hypogaea | Arach. hyp. | peanuts (groundnuts) |
| Beta vulgaris | — | sugarbeets |
| Bidens pilosa | — | — |
| Carthamus tinctorius | Carth. tinct. | safflower |
| Chenopodium album | Chen. alb. | common lambsquarters |
| Centaurea cyanus | — | cornflower |
| Cucumis sativus | Cucum. sat. | cucumber |
| Daucus carota | Dauc. car. | carrots |
| Desmodium tortuosum | Desmod. tort. | Florida beggarweed |
| Echinochloa crus galli | Echin. c.g. | barnyardgrass |
| Galinsoga parviflora | Galin. par. | gallant soldier |
| Gylcine max. | Glyc. max. | soybeans |
| Gossypium hirsutum | Gossyp. hirs. | cotton |
| Hordeum vulgare | Hord. vulg. | barley |
| Ipomoea spp. | Ipom. spp. | morningglory |
| Lactuca sativa | Lac. sat. | lettuce |
| Lamium spp. | — | dead-hettle |
| Lolium multiflorum | — | annual ryegrass |
| Matricaria spp. | Matr. | chamomile |
| Matricaria inodora | Matr. inod. | false chemomile |
| Mercurialis annua | Merc. ann. | annual mercury |
| Petroselinum spp. | Petr. spp. | parsley |
| Polygonum persicaria | Poly. per. | ladysthumb |
| Portulaca oleracea | Port. ol. | common purslane |
| Raphanua raphanistrum | Raph. | wild radish |
| Sesbania exaltata | Sesb. exalt. | hemp sesbania (coffeeweed) |
| Setaria viridis | Set. vir. | green foxtail |
| Setaria faberii | — | giant foxtail |
| Sinapis alba | Sinap. alba | white mustard |
| Solanum nigrum | — | black nightshade |
| Spergula arvensis | Sperg. arv. | corn spurry |
| Stellaria media | Stel. med. | chickweed |
| Thlaspi arvense | Thlas. arven. | field pennycress |
| Triticum aestivum | Tritic. aest. | wheat |
| Xanthium pensylvanicum | Xanth. pens. | common cocklebur |
| Zea mays | — | Indian corn |

Table 2

Herbicidal action of some new compounds; preemergence treatment in the greenhouse

| Active ingredient no. | kg/ha | Test plants and % damage | |
|---|---|---|---|
| | | Sesbania exaltata | Sinapis alba |
| 23 | 3.0 | — | 80 |
| 13 | 3.0 | — | 100 |
| 8 | 3.0 | 100 | — |
| 46 | 3.0 | 90 | — |
| 7 | 2.0 | — | 100 |

0 = no damage
100 = no emergence or plants destroyed

Table 3

Herbicidal action of some new compounds; postemergence treatment in the open

| Active ingredient no. | kg/ha | Alopec. myos | Anth./ Matr. | Chen. alb. | Echin. c.g. | Galin. par. | Poly. per. | Raph./ Sina. | Sperg. arv. | Thlas. arven. |
|---|---|---|---|---|---|---|---|---|---|---|
| 2 | 0.5 | 35 | 45 | 100 | 50 | 98 | 95 | 98 | 100 | 62 |
|   | 1.0 | 65 | 78 | 100 | 75 | 100 | 100 | 98 | 100 | 75 |
|   | 2.0 | 90 | 88 | 100 | 90 | 100 | 100 | 100 | 100 | 80 |
| 7 | 0.5 | 30 | 8 | 100 | 45 | 92 | 90 | 80 | 100 | 93 |
|   | 1.0 | 50 | 10 | 100 | 65 | 98 | 100 | 95 | 100 | 100 |
|   | 2.0 | 70 | 20 | 100 | 72 | 98 | 100 | 98 | 100 | 100 |
| 181 | 0.5 | 50 | 52 | 100 | 58 | 100 | 85 | 100 | 100 | 80 |
|   | 1.0 | 70 | 78 | 100 | 80 | 100 | 100 | 100 | 100 | 95 |
|   | 2.0 | 85 | 92 | 100 | 95 | 100 | 100 | 100 | 100 | 100 |

0 = no damage
100 = plants destroyed

Table 4

Selective herbicidal action of various compounds; postemergence treatment in the greenhouse

| Active ingredient no. | kg/ha | Arach. hyp. | Cucum. sat. | Dauc. car. | Glyc. max | Petr. spp. |
|---|---|---|---|---|---|---|
| 35 | 2.0 | 0 | 10 | 0 | 0 | 0 |
|  | 2.0 | 0 | 40 | 20 | 20 | 40 |

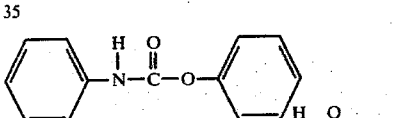

prior art

| Active ingredient no. | kg/ha | Amar. ret. | Chen. alb. | Merc. ann. | Sesb. exalt | Sinap. alba | Stell. media |
|---|---|---|---|---|---|---|---|
| 35 | 2.0 | 100 | 95 | 90 | 75 | 95 | 95 |
|  | 2.0 | 98 | 95 | 100 | 85 | 100 | 70 | prior art

0 = no damage
100 = plants destroyed

Table 5

Selective herbicidal action of various compounds; postemergence treatment in the greenhouse

| Active ingredient no. | kg/ha | Arach. hyp. | Glyc. max. | Gossyp. hirs. | Desmod. tort. | Sesb. exalt. | Xanth. penns. |
|---|---|---|---|---|---|---|---|
| 2 | 1.0 | 0 | 15 | 0 | 78 | 90 | 20 |
|  | 2.0 | 0 | 15 | 10 | 78 | 90 | 80 |
|  | 1.0 | 0 | 30 | 10 | 5 | 100 | 10 |
|  | 2.0 | 0 | 30 | 20 | 70 | 100 | 30 |

prior art

|  | 1.0 | 0 | 0 | 70 | 0 | 100 | 90 |
|---|---|---|---|---|---|---|---|
|  | 2.0 | 0 | 0 | 70 | 0 | 100 | 90 |

prior art

0 = no damage
100 = plants destroyed

Table 6

Selective herbicidal action of various compounds; postemergence treatment in the greenhouse

| Active ingredient no. | kg/ha | Arach. hyp. | Cucum. sat. | Dauc. car. | Gossyp. hirs. | Petr. spp. |
|---|---|---|---|---|---|---|
| 7 | 0.5 | — | 0 | 0 | 20 | 0 |
|  | 1.0 | 0 | — | 10 | 20 | 0 |
| 2 | 0.5 | — | 20 | 0 | 0 | 0 |
|  | 1.0 | 10 | 20 | 0 | 10 | 0 |
| 181 | 0.5 | — | 20 | 0 | 20 | 0 |
|  | 1.0 | 10 | 20 | 0 | 40 | 0 |

Table 6-continued

Selective herbicidal action of various compounds; postemergence treatment in the greenhouse

[Chemical structure: prior art compound — methylphenyl-NH-C(=O)-O-phenyl-NH-C(=O)-OCH₃]

prior art

| | | 0.5 | — | 40 | 35 | 25 | 10 |
| | | 1.0 | 0 | 50 | 45 | 45 | 85 |

| Active ingredient no. | kg/ha | Test plants and % damage |||||||
|---|---|---|---|---|---|---|---|
| | | Amar. ret. | Ipom. spp. | Merc. ann. | Port. ol. | Sesb. exalt | Set. vir. | Sinap. alba |
| 7 | 0.5 | 65 | 95 | 70 | 95 | 95 | 70 | 60 |
|  | 1.0 | 75 | 100 | 70 | 100 | 95 | 100 | 100 |
| 2 | 0.5 | 70 | 80 | 0 | 100 | 35 | 100 | 95 |
|  | 1.0 | 100 | 80 | 0 | 100 | 100 | 100 | 100 |
| 181 | 0.5 | 55 | 100 | 95 | 90 | 55 | 90 | 100 |
|  | 1.0 | 65 | 100 | 95 | 90 | 100 | 100 | 100 |
|  | 0.5 | 0 | 40 | 30 | 100 | 90 | 90 | 92 |
|  | 1.0 | 10 | 52 | 30 | 100 | 100 | 95 | 98 |

[Chemical structure: prior art compound]

prior art

0 = no damage
100 = plants destroyed

Table 7

Herbicidal action and tolerance by crop plants of various compounds, postemergence treatment in the greenhouse

| Active ingredient no. | kg/ha | Test plants and % damage ||||
|---|---|---|---|---|---|
| | | Arach. hyp. | Glyc. max. | Hord. vulg. | Lact. sat. |
| 184 | 2.0 | 0 | 0 | 0 | 0 |
|  | 2.0 | 0 | 10 | 25 | 30 |

[Chemical structure: prior art compound]

prior art

|  | 2.0 | 0 | 0 | 0 | 90 |

[Chemical structure: prior art compound with N-C₃H₇i, SO₂]

prior art

| Active ingredient no. | kg/ha | Test plants and % damage ||||||
|---|---|---|---|---|---|---|---|
| | | Tritic. aest. | Amar. ret. | Chen. alb. | Sesb. exalt | Sinap. alba | Stell. media |
| 184 | 2.0 | 0 | 80 | 80 | 100 | 90 | 80 |
|  | 2.0 | 60 | 30 | 95 | 90 | 100 | 90 |

[Chemical structure: prior art compound]

prior art

|  | 2.0 | 0 | 20 | 95 | 85 | 100 | 95 |

[Chemical structure: prior art compound with N-C₃H₇i, SO₂]

Table 7-continued

Herbicidal action and tolerance by crop plants of various compounds, postemergence treatment in the greenhouse prior art 0 = no damage
100 = plants destroyed

Table 8

Selective herbicidal action of various compounds; postemergence treatment in the greenhouse

| Active ingredient no. | kg/ha | Test plants and % damage | | | | | | | | |
|---|---|---|---|---|---|---|---|---|---|---|
| | | Arach. hyp. | Glyc. max. | Amar. ret. | Merc. ann. | Port. ol. | Sesb. exalt. | Set. vir. | Sinap. alba | Stell. media |
| 13 | 0.5 | — | 10 | 45 | 95 | 100 | 100 | 85 | 100 | 90 |
| | 1.0 | 10 | 10 | 50 | 95 | 100 | 100 | 85 | 100 | 90 |
| 8 | 0.5 | — | 0 | 98 | 40 | 100 | 70 | 100 | 50 | 80 |
| | 1.0 | 0 | 0 | 100 | 70 | 100 | 70 | 100 | 50 | 80 |
| (structure 1) | 0.5 | — | 0 | 0 | 60 | 100 | 90 | 90 | 90 | 90 |
| | 1.0 | 0 | 0 | 10 | 60 | 100 | 90 | 90 | 100 | 90 |
| prior art | | | | | | | | | | |
| (structure 2) | 0.5 | — | 0 | 0 | 40 | 100 | 85 | 10 | 100 | 95 |
| | 1.0 | 0 | 0 | 10 | 80 | — | 85 | 40 | 100 | 95 |
| prior art | | | | | | | | | | |

Structure 1 (prior art): 3-methylphenyl-NH-C(O)-O-phenyl-NH-C(O)-OCH₃

Structure 2 (prior art): benzoyl-N(C₃H₇i)-SO₂-NH (fused ring system)

0 = no damage
100 = plants destroyed

Table 9

Tolerance by sugarbeets and herbicidal action of various compounds; postemergence treatment in climatic cabinet

| Active ingredient no. | kg/ha | Test plants and % damage Temperature ranges °C. | | | |
|---|---|---|---|---|---|
| | | Sugarbeets | | Sinapis alba | |
| | | 11 | 22 | 11 | 22 |
| 2 | 0.5 | 0 | 0 | 70 | 92 |
| | 1.0 | 12 | 2 | 75 | 92 |
| | 2.0 | 10 | 2 | 85 | 100 |
| (structure) | 0.5 | 0 | 10 | 88 | 95 |
| | 1.0 | 0 | 10 | 90 | 100 |
| | 2.0 | 7 | 10 | 90 | 100 |

Structure (prior art): phenyl-NH-C(O)-O-phenyl(CH₃)-NH-C(O)-O-CH₃ prior art

0 = no damage
100 = plants destroyed

Table 10

Selective herbicidal action of new diurethanes; postemergence treatment in the greenhouse

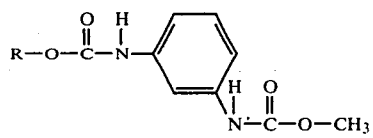

| Active ingredient no. | Substituent R | kg/ha | Arach. hyp. | Carth. tinct. | Dauc. car. | Hord. vulg. | Tritic aest. | Zea mays | Desmod. tort. | Sesb. exalt. | Sinap. alba. | Stell. med. |
|---|---|---|---|---|---|---|---|---|---|---|---|---|
|  | (structure: CH3, H3C, H5C2O-furan) | 1.0 | 10 | 0 | 0 | 0 | 0 | 10 | 100 | 90 | 99 | 30 |
|  |  | 2.0 | 20 | 0 | 0 | 0 | 0 | 15 | 100 | 95 | 99 | 70 |
| 90 |  | 1.0 | 0 | 0 | 0 | 0 | 0 | 0 | 100 | 95 | 75 | 100 |
|  |  | 2.0 | 0 | 0 | 0 | 0 | 0 | 0 | 100 | 95 | 95 | 100 |
| 82 |  | 1.0 | 0 | 0 | 0 | 0 | 0 | 0 | 100 | 95 | 99 | 100 |
|  |  | 2.0 | 0 | 0 | 0 | 0 | 0 | 0 | 100 | 95 | 100 | 100 |
| 105 |  | 1.0 | 0 | 0 | 0 | — | 0 | 0 | 100 | 45 | 100 | — |
|  |  | 2.0 | 0 | 0 | 0 | — | 0 | 0 | 100 | 50 | 100 | — |
| 172 |  | 1.0 | 0 | 0 | — | 0 | — | 0 | 30 | 50 | 60 | 100 |
|  |  | 2.0 | 20 | 0 | — | 0 | 0 | 0 | 100 | 60 | 100 | — |

0 = no damage
100 = plants destroyed

Table 11

Preemergence action of new diurethanes; greenhouse application

| Active ingredient no. | Compounds | kg/ha | Amar. ret. | Bidens pilosa | Matr. inod. | Sinap. alba | Solanum nigrum | Stell. med. |
|---|---|---|---|---|---|---|---|---|
| 85 |  | 1.0 | 90 | 100 | 100 | 98 | 65 | 98 |
|  |  | 2.0 | 95 | 100 | 100 | 98 | 90 | 98 |
|  | (prior art diurethane structure) | 1.0 | 0 | 10 | 40 | 40 | 10 | 50 |
|  |  | 2.0 | 0 | 50 | 75 | 50 | 15 | 70 |
|  | (prior art pyridazinone structure) | 1.0 | 60 | 95 | 100 | 95 | 55 | 60 |
|  |  | 2.0 | 80 | 100 | 100 | 95 | 70 | 70 |

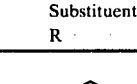

0 = no damage
100 = plants destroyed

Table 12

Tolerance by various soybean species; postemergence application in the greenhouse

| Active ingredient no. | Compound | kg/ha | SRF 450 | Dare | Lee 68 | Bragg | Prata | Prenola | Planato | Setaria[x] faberii | Sesb.[x] exalt. | Stell. media |
|---|---|---|---|---|---|---|---|---|---|---|---|---|
| 8 |  | 0.5 | 0 | 0 | 0 | 0 | 0 | 0 | 0 | 10 | 60 | 40 |
| 8 | + linseed oil emulsified in water in amount of 4 vol % of spray liquor | 0.5 | 0 | 10 | 0 | 15 | 0 | 0 | 0 | 100 | 95 | 100 |

Table 12-continued

Tolerance by various soybean species; postemergence application in the greenhouse

| Active ingredient no. | Compound | kg/ha | % damage in soybean species and other test plants ||||||||||
|---|---|---|---|---|---|---|---|---|---|---|---|---|
| | | | SRF 450 | Dare | Lee 68 | Bragg | Prata | Prenola | Planato | Setaria$^x$ faberii | Sesb.$^x$ exalt. | Stell. media |
| | 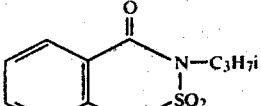 prior art | 0.5 | 0 | 0 | 0 | 0 | 0 | 0 | 0 | 0 | 40 | 100 |
| | 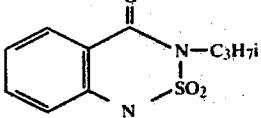 | 0.5 | 0 | 10 | 0 | 0 | 10 | 10 | 10 | 0 | 80 | 100 |

+ linseed oil emulsified in water in amount of 4 vol % of spray liquor

0 = no damage
100 = plants destroyed
$^x$ larger plants than in Table 8

Table 13

Selective herbicidal action in beets; postemergence treatment in the greenhouse

| Active ingredient no. | Compound | kg/ha | Test plants and % damage ||||||
|---|---|---|---|---|---|---|---|---|
| | | | Beta vulg. | Hord. vulg. | Chen. alb. | Lamium spp. | Merc. annua | Sinapis alba |
| 101 | | 1.0 | 0 | 0 | 80 | 100 | 80 | 98 |
| | | 2.0 | 0 | 0 | — | 100 | 100 | 100 |

0 = no damage
100 = plants destroyed

Table 14

Herbicidal action of new compounds, preemergence (PRE) and postemergence (POST) treatment in greenhouse

| Active ingredient no. | kg/ha | Test plants and % damage ||||
|---|---|---|---|---|---|
| | | Centaurea cyanus | Ipomoea spp. | Lolium multiflorum | Sinapis alba |
| 204 | 3.0 PRE | — | 0 | 0 | 100 |
| | 3.0 POST | 100 | 0 | 95 | — |
| 209 | 3.0 PRE | — | 0 | 10 | 80 |
| | 3.0 POST | 100 | 100 | 40 | — |
| 205 | 3.0 PRE | — | 0 | 0 | 0 |
| | 3.0 POST | 80 | 80 | 40 | 0 |
| 212 | 3.0 PRE | — | 0 | 0 | 0 |
| | 3.0 POST | 80 | 20 | 40 | — |
| 199 | 3.0 PRE | — | 0 | 0 | 40 |
| | 3.0 POST | 80 | 60 | 40 | — |
| 202 | 3.0 PRE | — | 40 | 80 | 80 |
| | 3.0 POST | 80 | 80 | 80 | — |
| 201 | 3.0 PRE | — | 0 | 20 | 0 |
| | 3.0 POST | 80 | 80 | 80 | — |
| 216 | 3.0 PRE | — | 80 | 50 | 40 |
| | 3.0 POST | 100 | 100 | 90 | — |

0 = no damage
100 = plants destroyed

The new active ingredients may be incorporated into the soil, or applied to the surface of the soil or to emerged plants. It is also possible to eliminate unwanted plants by post-directed or lay-by applications. In this case, the spray is directed in such a manner that the leaves of sensitive crop plants are not—or only slightly—touched, and the soil and smaller weeds are fully contacted.

In view of the application possibilities, the herbicides according to the invention or compositions containing them may not only be used in the crops listed in the tables but also in a much wider range of crops for removing unwanted plants. The amount of active ingredient applied may vary from 0.1 to 15 kg/ha and more, depending on the weeds to be controlled. The following crops may be mentioned by way of example:

| Botanical name | Common name |
|---|---|
| Allium cepa | onions |
| Ananas comosus | pineapple |
| Asparagus officinalis | asparagus |
| Avena sativa | oats |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Citrus limon | lemon |
| Citrus maxima | grapefruit |
| Citrus reticulata | |
| Citrus sinensis | orange trees |
| Coffea arabica (Coffea canephora, Coffea liberica) | coffee plants |
| Cucumis melo | melons |
| Cynodon dactylon | Bermudagrass in turf and lawns |

-continued

| Botanical name | Common name |
|---|---|
| Elaeis guineensis | oil palms |
| Fragaria vesca | strawberries |
| Gossypium arboreum | } cotton |
| Gossypium herbaceum | |
| Gossypium vitifolium | |
| Helianthus annuus | sunflowers |
| Helianthus tuberosus | |
| Hevea brasiliensis | rubber plants |
| Humulus lupulus | hops |
| Ipomoea batatas | sweet potato |
| Lens culinaris | lentils |
| Linum usitatissimum | flax |
| Lycopersicon lycopersicum | tomato |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | |
| Phaseolus lunatus | limebeans |
| Phaseolus mungo | mungbeans |
| Phaseolus vulgaris | snapbeans, green beans, dry beans |
| Pennisetum glaucum | |
| Picea abies | |
| Pinus | pine trees |
| Pisum sativum spp. sativum | English peas |
| Prunus avium | cherry trees |

-continued

| Botanical name | Common name |
|---|---|
| Prunus domestica | plum trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Secale cereale | rye |
| Solanum tuberosum | Irish potatoes |
| Sorghum bicolor (S. vulgare) | grain sorghum |
| Sorghum dochna | |
| Spinacia oleracea | spinach |
| Theobroma cacao | cacao plants |
| Trifolium pratense | red clover |
| Vaccinium corymbosum | blueberry |
| Vaccinium vitis-idaea | cranberry |
| Vicia faba | tick beans |
| Vigna sinensis (V. unguiculata) | cow peas |
| Vitis vinifera | grapes |
| Zea mays | Indian corn, sweet corn, maize |

To broaden the spectrum of action of the new individual compounds, to achieve synergistic effects or to improve persistence in the soil, the compounds according to the invention may be mixed with each other, and numerous other herbicidal and growth-regulating compounds may be used as mixture and combination components. Depending on area of use and objective, the following substances or similar derivatives may be used in mixtures:

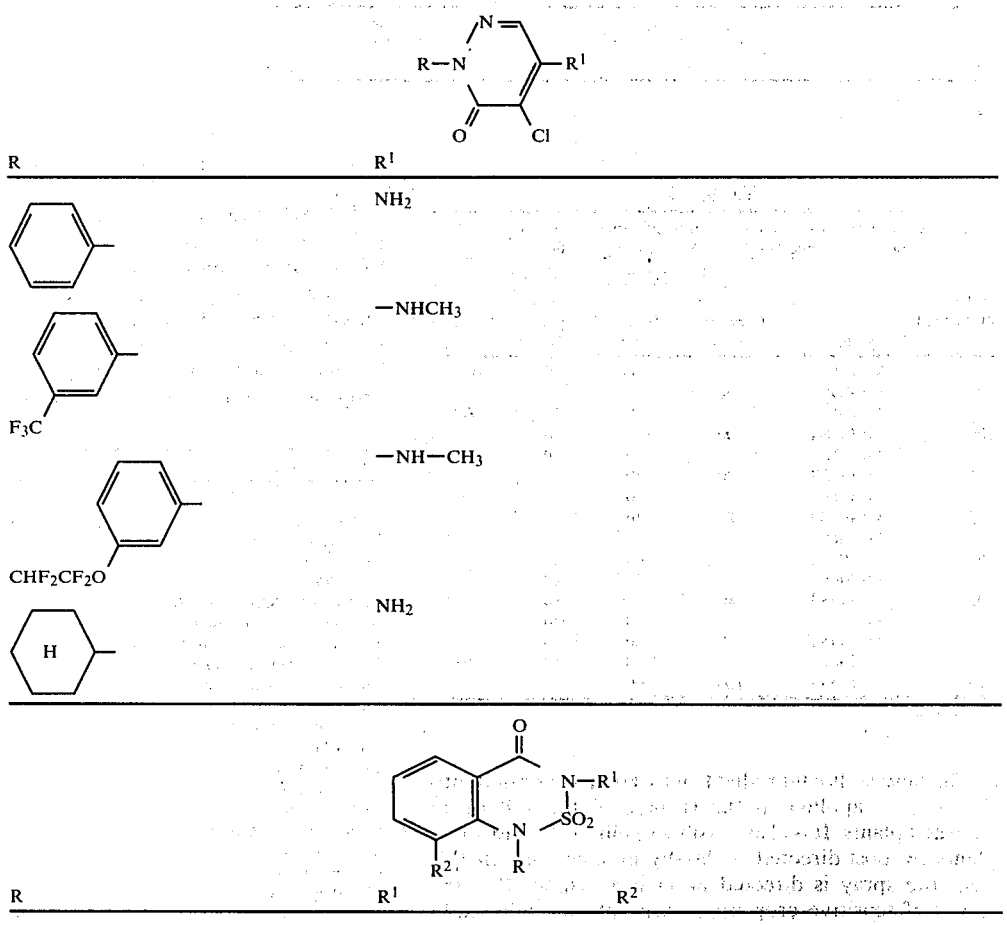

-continued
| | | |
|---|---|---|
| H |  | H and salts |
| H |  | Cl and salts |
| H |  | F and salts |
| H |  | $CH_3$ and salts |
| $CH_2OCH_3$ |  | H |
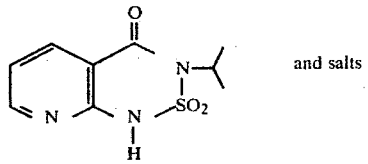 and salts
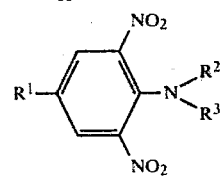
| $R^1$ | $R^2$ | $R^3$ |
|---|---|---|
| $CF_3$ | n . $C_3H_7$ | n . $C_3H_7$ |
| $CF_3$ | n . $C_3H_7$ | $CH_2-CH_2Cl$ |
| $SO_2NH_2$ | n . $C_3H_7$ | n . $C_3H_7$ |
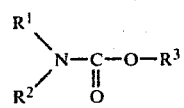
| $R^1$ | $R^2$ | $R^3$ |
|---|---|---|
| $CH_3$ | H | 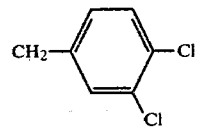 |
| 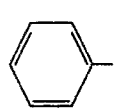 | H | i-$C_3H_7$ |
| 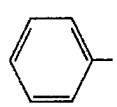 | H | 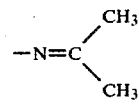 |
| 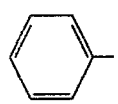 | H | 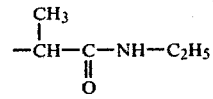 |
| 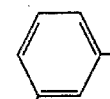 | H | i-$C_3H_7$ |
| 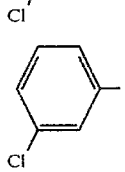 | H | $CH_2-C\equiv C-CH_2Cl$ |

-continued
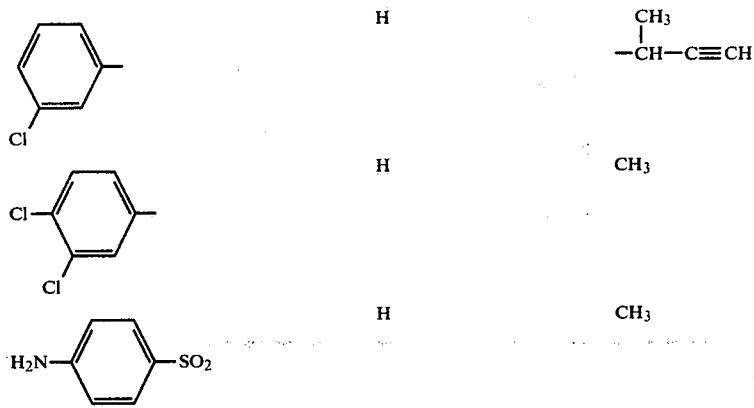
| | H | CH₃ |
| | | -CH-C≡CH |
| | | | |
| | | CH₃ (on -CH-) |
| | H | CH₃ |
| | H | CH₃ |
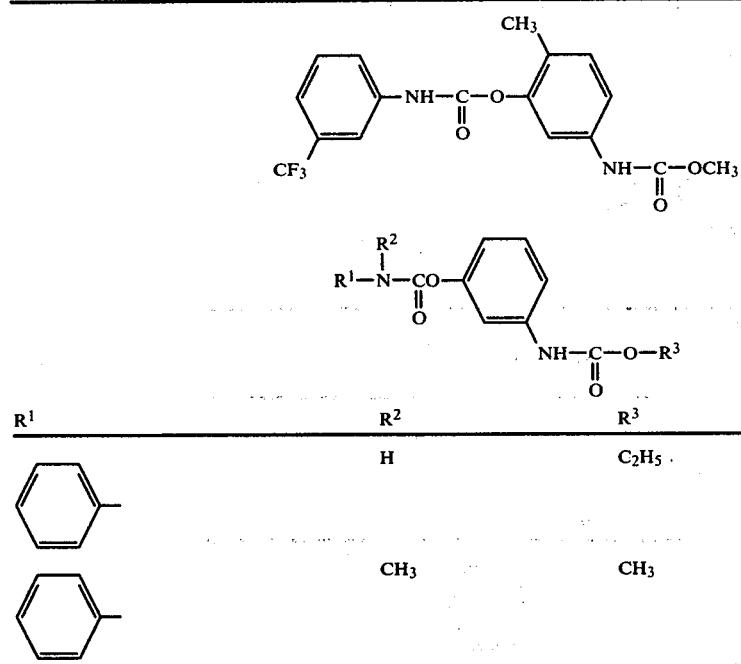
| R¹ | R² | R³ |
|---|---|---|
| phenyl | H | C₂H₅ |
| phenyl | CH₃ | CH₃ |
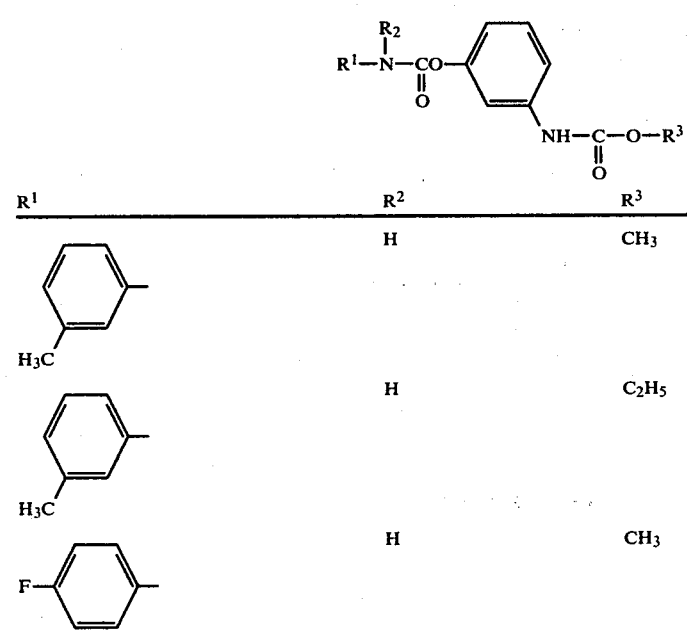
| R¹ | R² | R³ |
|---|---|---|
| 3-methylphenyl | H | CH₃ |
| 3-methylphenyl | H | C₂H₅ |
| 4-fluorophenyl | H | CH₃ |

-continued
| | | |
|---|---|---|
| 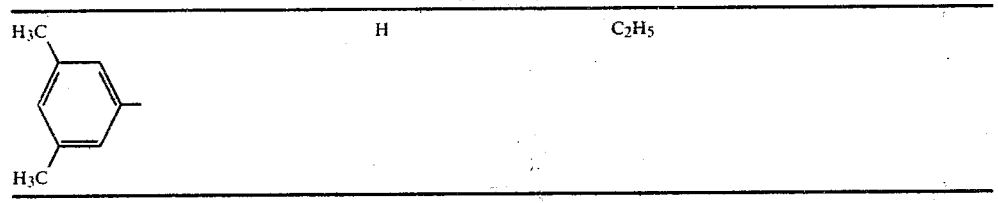 | H | C₂H₅ |
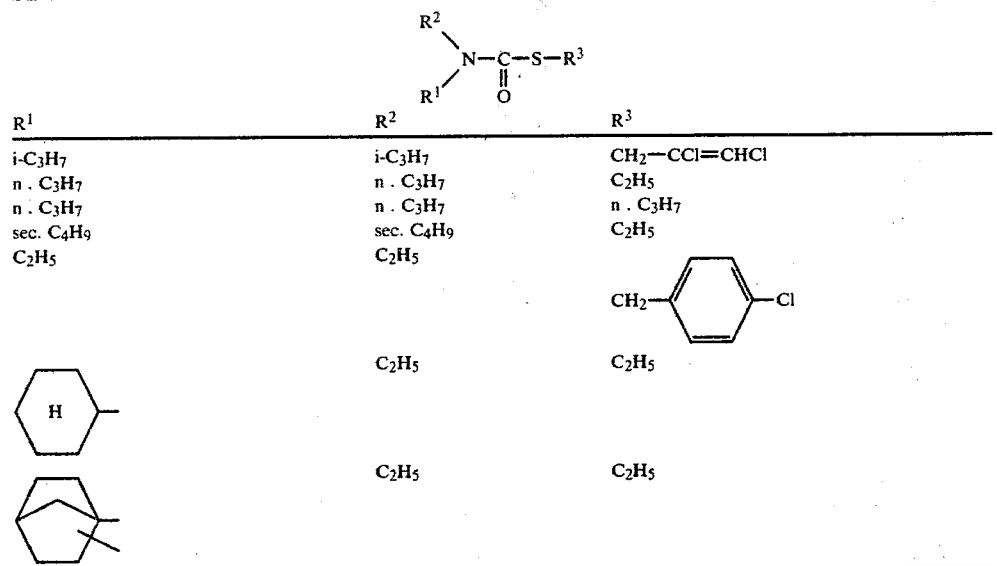
| R¹ | R² | R³ |
|---|---|---|
| i-C₃H₇ | i-C₃H₇ | CH₂—CCl=CHCl |
| n.C₃H₇ | n.C₃H₇ | C₂H₅ |
| n.C₃H₇ | n.C₃H₇ | n.C₃H₇ |
| sec. C₄H₉ | sec. C₄H₉ | C₂H₅ |
| C₂H₅ | C₂H₅ | |
| | C₂H₅ | C₂H₅ |
| | C₂H₅ | C₂H₅ |
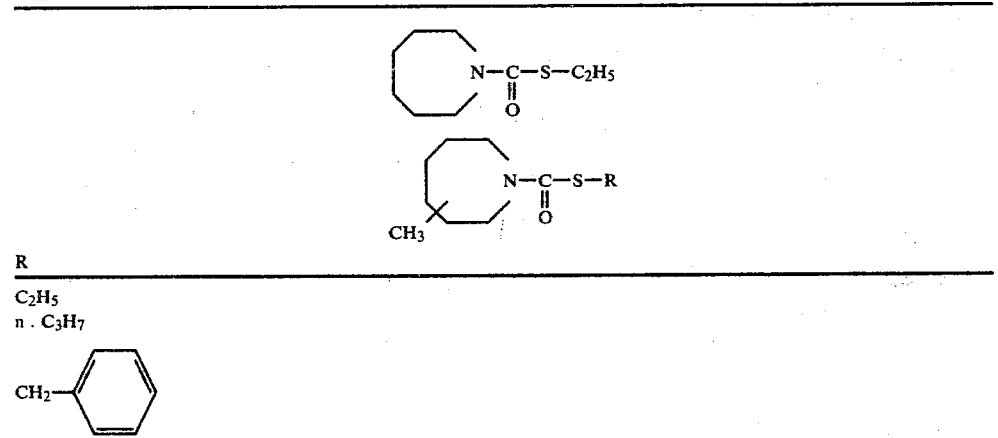
| R |
|---|
| C₂H₅ |
| n.C₃H₇ |
| |
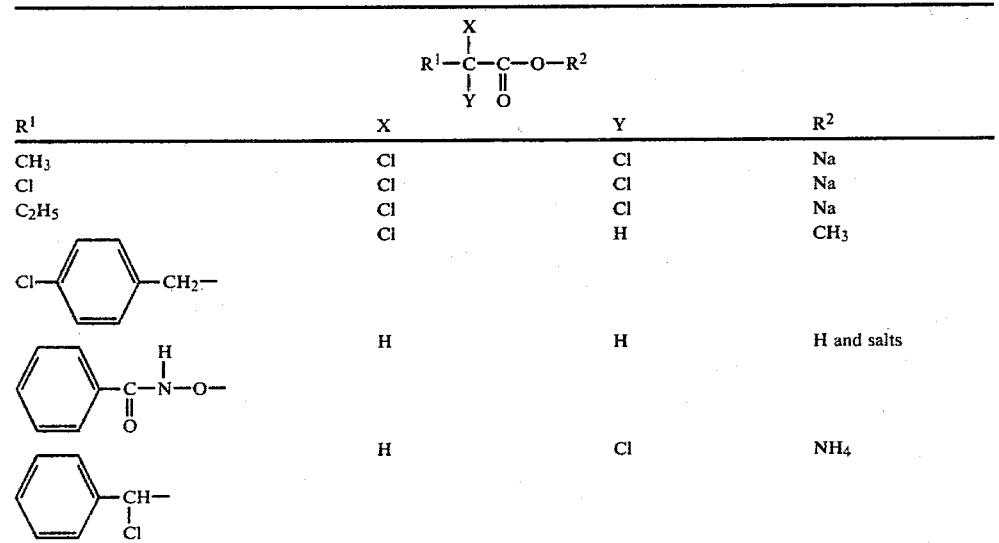
| R¹ | X | Y | R² |
|---|---|---|---|
| CH₃ | Cl | Cl | Na |
| Cl | Cl | Cl | Na |
| C₂H₅ | Cl | Cl | Na |
| | Cl | H | CH₃ |
| | | | |
| | H | H | H and salts |
| | H | Cl | NH₄ |

-continued
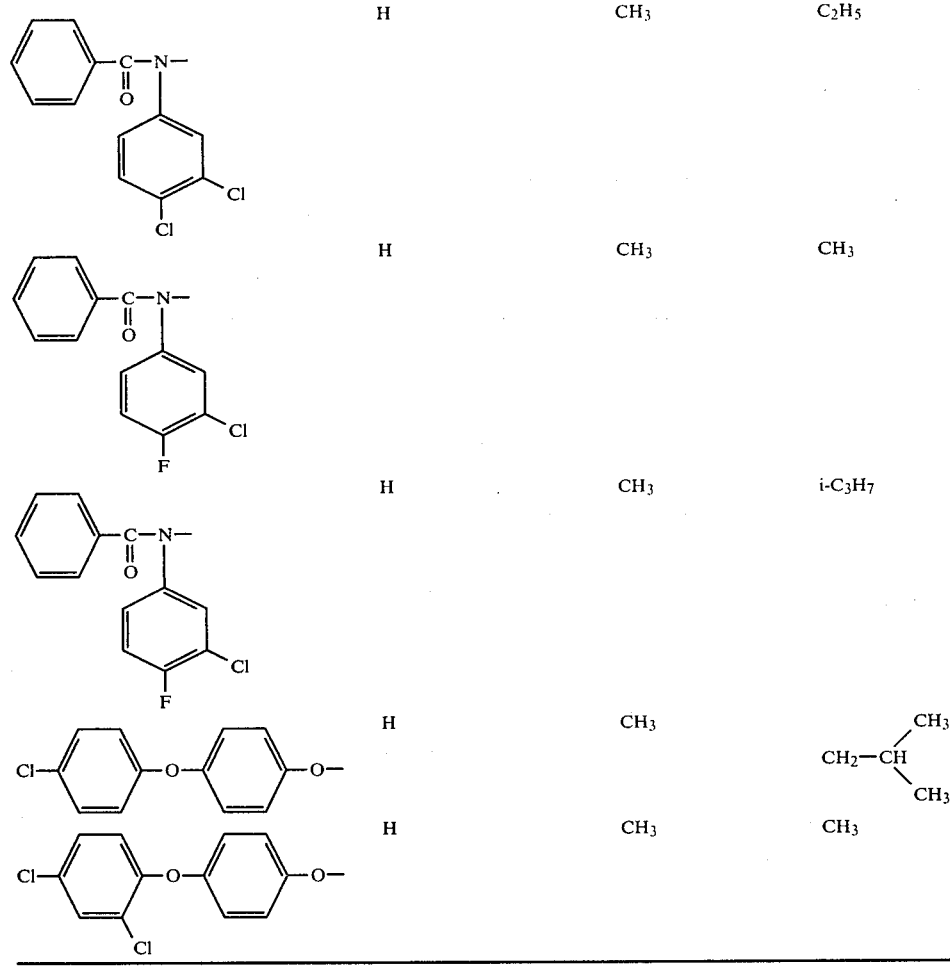
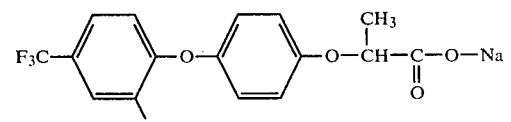
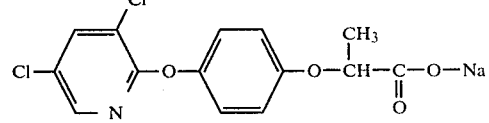
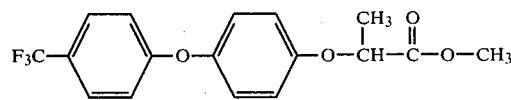
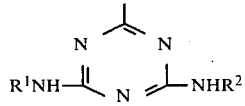
| R¹ | X | R² |
|---|---|---|
| i-C₃H₇ | Cl | C₂H₅ |
| i-C₃H₇ | Cl | ▷ |
| i-C₃H₇ | Cl | i-C₃H₇ |
| C₂H₅ | Cl | C₂H₅ |
| C₂H₅ | Cl | —C(CH₃)₂CN |
| C₂H₅ | Cl | —CH—CH₂—OCH₃<br>    \|<br>   CH₃ |

-continued

| | | |
|---|---|---|
| C$_2$H$_5$ | Cl | —CH(CH$_3$)—C≡CH |
| cyclopropyl | Cl | —C(CH$_3$)$_2$—CN |
| i-C$_3$H$_7$ | OCH$_3$ | i-C$_3$H$_7$ |
| i-C$_3$H$_7$ | SCH$_3$ | C$_2$H$_5$ |
| C$_2$H$_5$ | SCH$_3$ | C$_2$H$_5$ |
| C$_2$H$_5$ | SCH$_3$ | tert. C$_4$H$_9$ |

| X | Y | R |
|---|---|---|
| CF$_3$ | H | CH$_3$ |
| H | F | CH$_3$ |

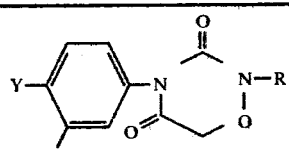

| R$^1$ | R$^2$ | R$^3$ |
|---|---|---|
| phenyl | —CH(CH$_3$)—C≡CH | CH$_2$Cl |
| 3-ethyl-2-methylphenyl | —CH(CH$_3$)—CH$_2$—OCH$_3$ | CH$_2$Cl |
| 3-ethyl-2-methylphenyl | —CH$_2$—CH$_2$—OCH$_3$ | CH$_2$Cl |
| 2,6-dimethyl-3-ethylphenyl | —CH$_2$—OCH$_3$ | CH$_2$Cl |
| 2,6-diethylphenyl | —CH$_2$—C(=O)—OC$_2$H$_5$ | CH$_2$Cl |
| 2,6-diethylphenyl | —CH$_2$—O—C$_4$H$_9$n | CH$_2$Cl |
| 2,6-dimethylphenyl | —CH$_2$-(1,3-dioxolan-2-yl) | CH$_2$Cl |

-continued
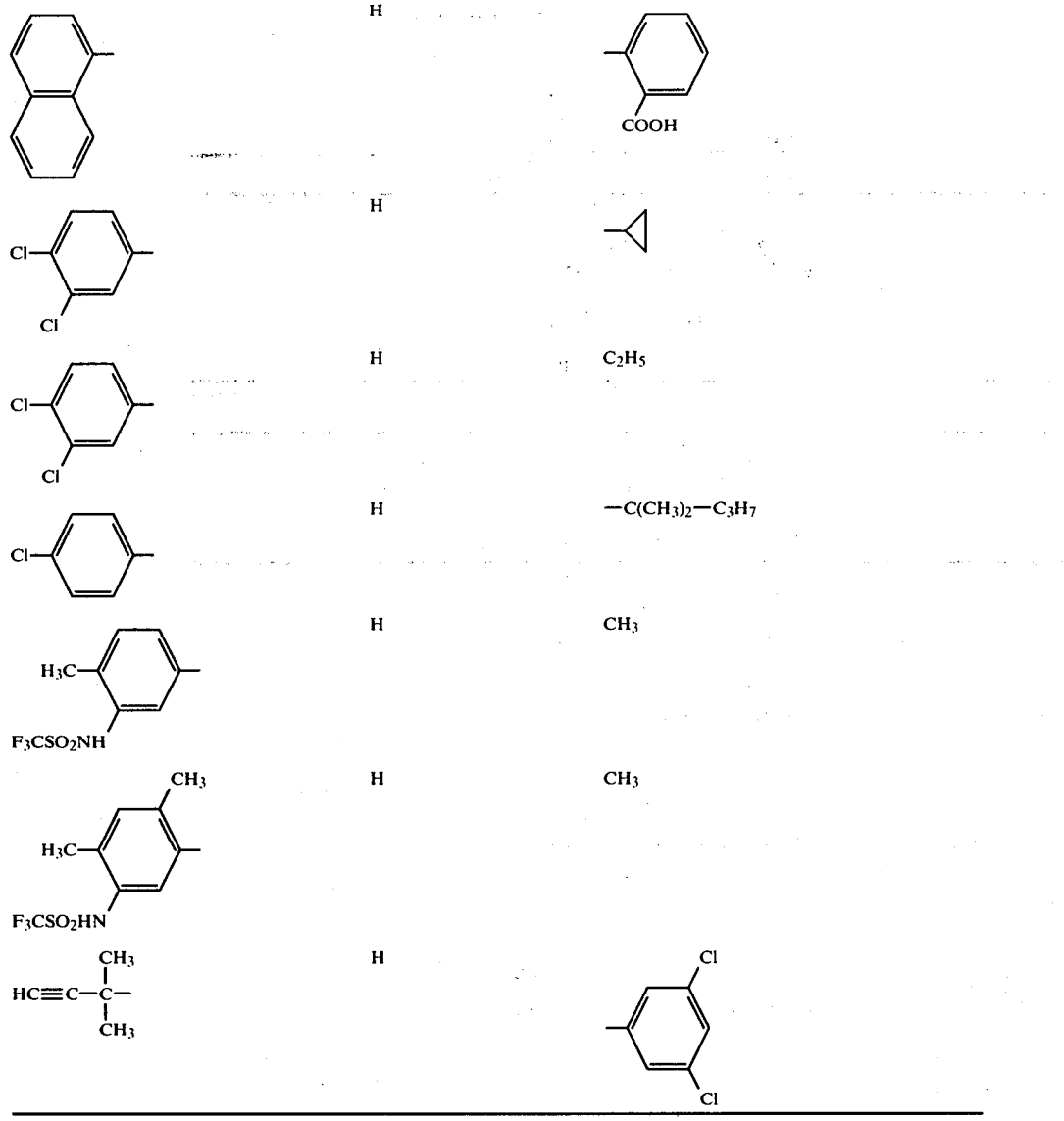
| X | X₁ | R |
|---|----|---|
| Br | Br | H and salts |
| J | J | H and salts |
| Br | Br | —C(O)—(CH₂)₆—CH₃ |

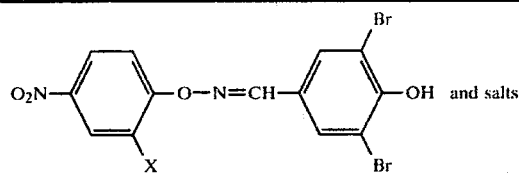

X = NO₂
CN

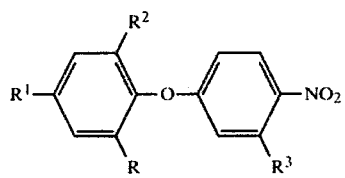

| R | R¹ | R² | R³ |
|---|---|---|---|
| Cl | Cl | Cl | H |
| F | Cl | Cl | H |
| Cl | Cl | H | H |
| Cl | CF₃ | H | COOH |
| Cl | Cl | H | COOCH₃ |
| NO₂ | CF₃ | H | H |
| H | CF₃ | Cl | H |
| H | CF₃ | Cl | OC₂H₅ |
| Cl | Cl | H | OCH₃ |

$$\begin{array}{c} R^2 \\ | \\ R^1 \end{array} N - \underset{\underset{O}{\|}}{C} - N \begin{array}{c} R^3 \\ | \\ R^4 \end{array}$$

| R¹ | R² | R³ | R⁴ |
|---|---|---|---|
| 4-isopropylphenyl | H | CH₃ | CH₃ |
| 3-chloro-4-methoxyphenyl | H | CH₃ | CH₃ |
| 3-(tert-H₉C₄HN—CO)phenyl | H | CH₃ | CH₃ |
| phenyl | H | CH₃ | CH₃ |
| 3,4-dichlorophenyl | H | CH₃ | CH₃ |
| 4-chlorophenyl | H | CH₃ | —CH(CH₃)—C≡CH |
| 3-trifluoromethylphenyl | H | CH₃ | CH₃ |

-continued
| | | | |
|---|---|---|---|
| 4-Br-C6H4- | H | CH3 | OCH3 |
| 3-Cl-4-CH3-C6H3- | H | CH3 | CH3 |
| 4-Cl-C6H4- | H | CH3 | OCH3 |
| 2-Cl-4-(ClCF2S)-C6H3- | H | CH3 | CH3 |
| 4-Cl-C6H4- | H | CH3 | CH3 |
| 3,4-Cl2-C6H3- | H | CH3 | OCH3 |
| 4-(4-Cl-C6H4-O)-C6H4- | H | CH3 | CH3 |
| 3-Cl-4-Br-C6H3- | H | CH3 | OCH3 |
| 3-Cl-4-OCH3-C6H3- | H | CH3 | OCH3 |
| 3,5-Cl2-4-OCH3-C6H2- | H | CH3 | CH3 |
| 2-benzothiazolyl | CH3 | H | CH3 |
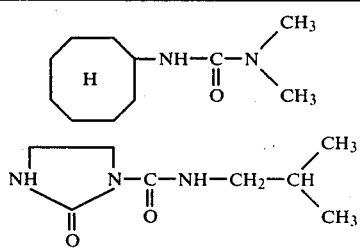

-continued
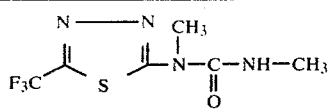
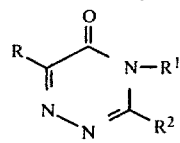
| R | R¹ | R² |
|---|---|---|
| tert. C₄H₉ | NH₂ | SCH₃ |
| tert. C₄H₉ | $-N=CH-CH\begin{smallmatrix}CH_3\\CH_3\end{smallmatrix}$ | SCH₃ |
| 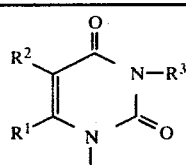 | NH₂ | CH₃ |
| R¹ | R² | R³ |
|---|---|---|
| CH₃ | Br | sec. C₄H₉ |
| CH₃ | Cl | tert. C₄H₉ |
| CH₃ | Cl | 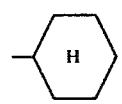 |
| | -CH₂-CH₂-CH₂- | |
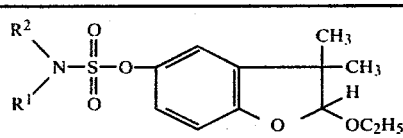
| R¹ | R² |
|---|---|
| CH₃ | CH₃ |
| CH₃ | $-\underset{\underset{O}{\|\|}}{C}-CH_3$ |
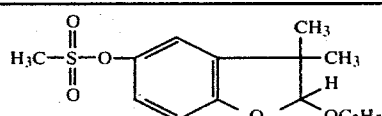
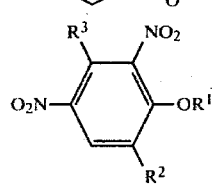
| R¹ | R² | R³ |
|---|---|---|
| $-\underset{\underset{O}{\|\|}}{C}-CH_3$ | sec. C₄H₉ | H |
| $-\underset{\underset{O}{\|\|}}{C}-CH_3$ | tert. C₄H₉ | H |

-continued
| | | | |
|---|---|---|---|
| —C(=O)—CH₃ | tert. C₄H₉ | CH₃ | |
| H | CH₃ | H | salts and esters |
| H | sec. C₄H₉ | H | salts and esters |
| H | tert. C₄H₉ | H | salts and esters |
| H | tert. C₄H₉ | CH₃ | salts and esters |
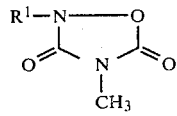
| R¹ |
|---|
| 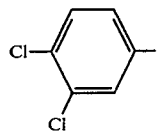 |
| 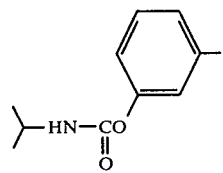 |
| 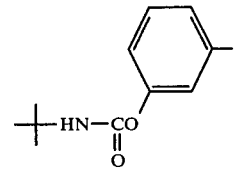 |
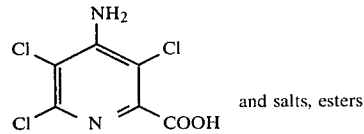 and salts, esters
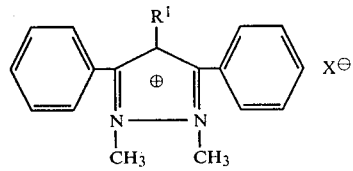
| R¹ | X |
|---|---|
| H | CH₃OSO₃ |
| Br | CH₃OSO₃ |
| CH₃ | CH₃OSO₃ |
| CH₃ | CF₃SO₃ |
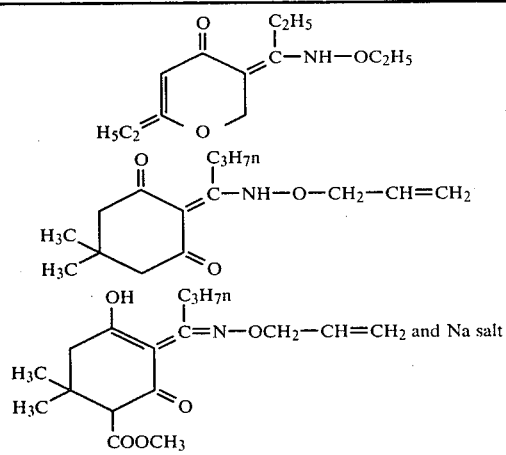

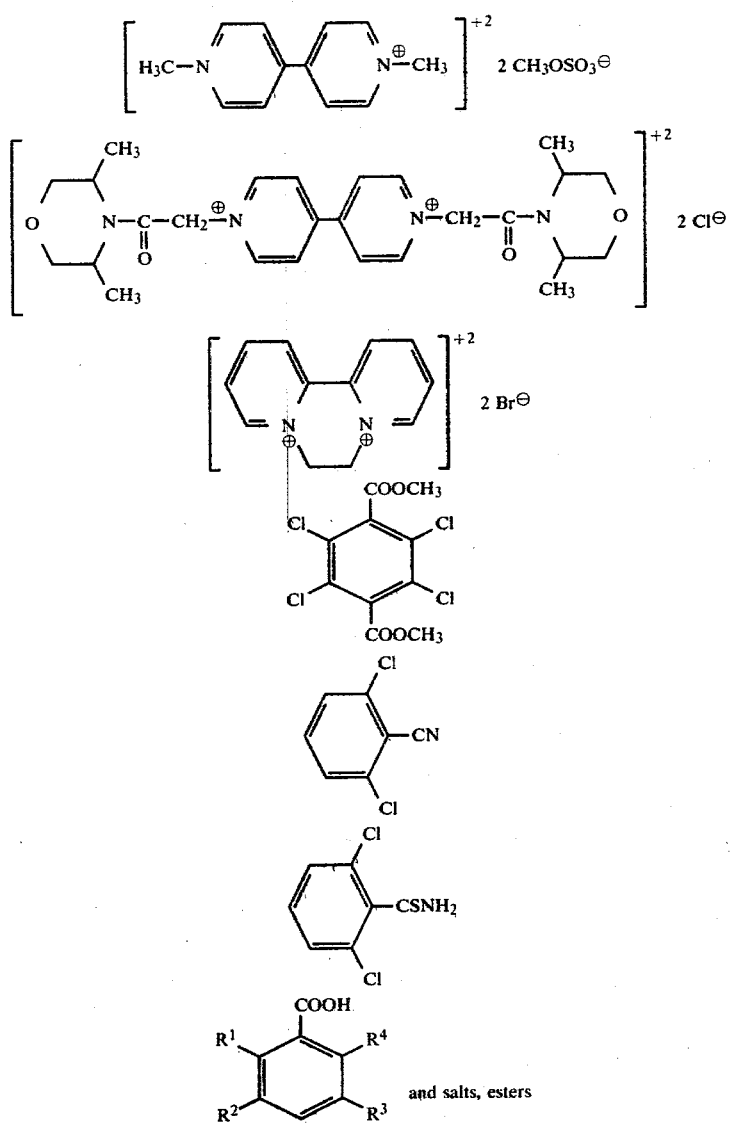

-continued
| | | | |
|---|---|---|---|
| 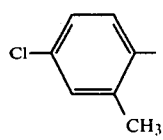 | H | H | salts, esters, amides |
| 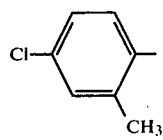 | CH$_3$ | H | salts, esters, amides |
| 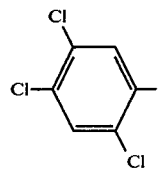 | H | H | salts, esters, amides |
| 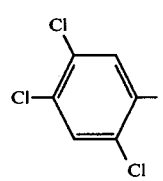 | CH$_3$ | H | salts, esters, amides |
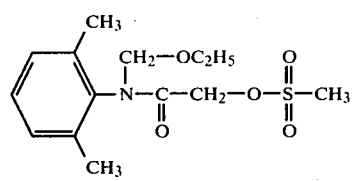
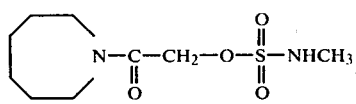
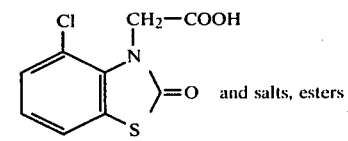 and salts, esters
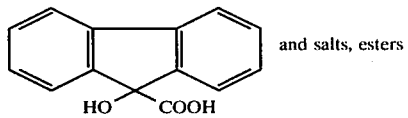 and salts, esters
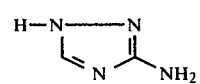
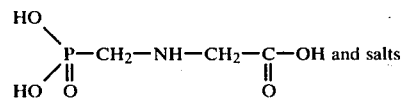 and salts
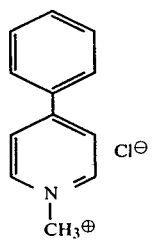

-continued

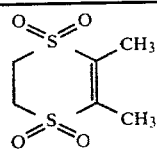

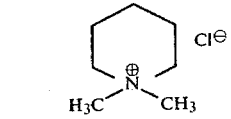

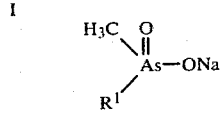

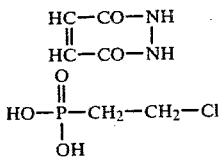

| $R^1$ |
| --- |
| OH |
| $CH_3$ |

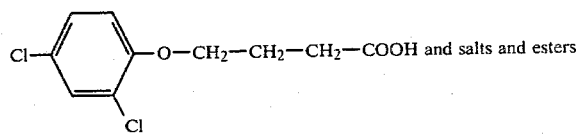

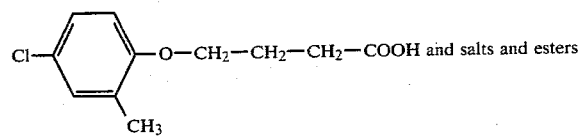

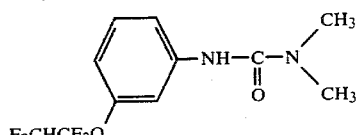

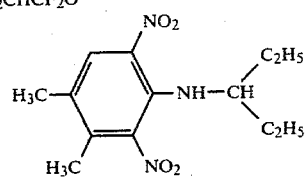

It is also possible to apply the compounds of the invention either alone or in combination with other herbicides, in admixture with other crop protection agents, for example agents for combatting pests or phytopathogenic fungi or bacteria. Of further interest is the fact that the compounds of the invention may be mixed with solutions of mineral fertilizers used to eliminate trace element or nutritional deficiencies.

Spreader-stickers and non-phytotoxic oils may be added to the compounds of the invention to ensure that they take effect.

The new compounds have a good fungicidal action for example on phytopathogenic fungi, especially rusts, for instance in cereals and beans. The following fungi for example may be controlled: *Puccinia coronata* in oats, *Puccinia hordei* in barley, *Puccinia striiformis* and *Puccinia recondita* in wheat, and *Uromyces fabae* and *Uromyces appendiculatus* in beans.

Application rates are from 0.2 to 1 kg of active ingredient per hectare.

EXAMPLE 2

Leaves of barley plants of the Asse variety and wheat plants of the Caribo variety, grown in pots, are artificially infected with spores of *Puccinia hordei* or *Puccinia recondita*, and the plants are placed for 24 hours in a steam-saturated chamber at 20° to 25° C. The plants are then sprayed with aqueous spray liquors containing (dissolved or emulsified in the water) a mixture of 80% of the active ingredient to be examined and 20% of lignin sulfate, and placed in the greenhouse at from 20° to 22° C. and a relative humidity of from 75 to 80%. The extent to which the rust fungus has spread is assessed after 10 days.

| Active ingredient | Attack after spraying with liquor containing 0.05% active ingredient | |
|---|---|---|
| | Puccinia hordei | Puccinia recondita |
| 7 | 0 | 0 |
| 2 | 0 | 0 |
| 8 | 0 | 0 |
| prior art (German Laid-Open Application DOS 1,567,211) | 1 | 2 |
| Control (untreated) | 5 | |

0 = no attack, graduated down to 5 = 100% attack

EXAMPLE 3

As described in Example 2, leaves of oat plants of the Flämingskrone variety grown in pots are artificially infected with spores of *Puccinia coronata*, and sprayed with aqueous suspensions of the active ingredients given in the Table.

| Active ingredient | Attack after spraying with liquor containing 0.05% active ingredient |
|---|---|
| 2 | 0 |
| 8 | 0 |
| prior art (German Laid-Open Application DOS 1,567,211) | 1-2 |
| Control (untreated) | 5 |

EXAMPLE 4

As described in Example 2, leaves of bean plants of the Mombacher Speck variety grown in pots are artificially infected with spores of *Uromyces fabae*, and treated with aqueous suspensions of the active ingredients given in the Table.

| Active ingredient | Attack after spraying with liquor containing 0.05% active ingredient |
|---|---|
| 7 | 1-2 |
| 8 | 0 |
| 2 | 2 |
| prior art (German Laid-Open Application DOS 1,567,211) | |
| Control (untreated) | 5 |

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalene-sulfonic acids, phenolsulfonic acids, alkylaryl sulfonates, alkyl sulfates, and alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products or sulfonated naphthalene and naphthalene derivatives with formaldehyde, condensation products of naphthalene or naphthalenesulfonic acids with phenol and formaldehyde, polyoxyethylene octylphenol esters, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phospate, ammonium nitrate, and ureas, and vegetable products such as grain flours, bark meal, wood meal, and nutshell meal, cellulosic powders, etc.

The formulations contain from 0.1 to 95, and preferably 0.5 to 90%, by weight of active ingredient.

EXAMPLE 5

90 parts by weight of compound 2 is mixed with 10 parts by weight of N-methyl-α-pyrrolidone. A mixture is obtained which is suitable for application in the form of very fine drops.

EXAMPLE 6

20 parts by weight of compound 8 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 13 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound 23 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 7 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 10

3 parts by weight of compound 46 is intimately mixed with 97 parts by weight of particulate kaolin. A dust is obtained containing 3% by weight of the active ingredient.

EXAMPLE 11

30 parts by weight of compound 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 12

40 parts by weight of compound 7 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 13

20 parts of compound 8 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A diurethane of the formula

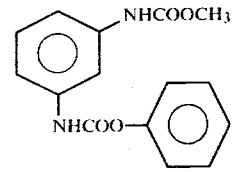

2. A diurethane of the formula

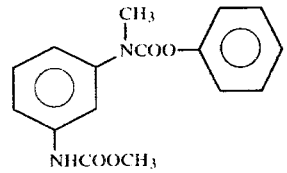

3. A diurethane of the formula

4. A diurethane of the formula

5. A diurethane of the formula
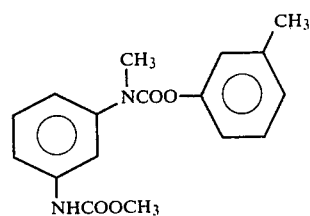
6. A diurethane of the formula
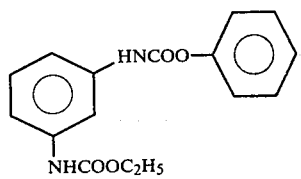
7. A diurethane of the formula
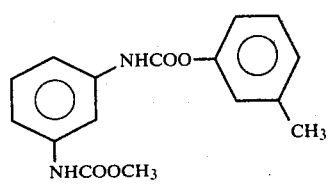
8. A diurethane of the formula
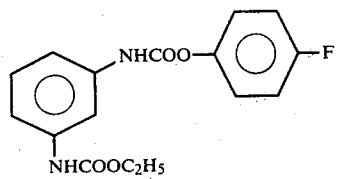
9. A diurethane of the formula
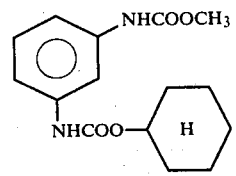
* * * * *